(12) United States Patent
Choi

(10) Patent No.: US 11,901,075 B2
(45) Date of Patent: Feb. 13, 2024

(54) METHOD AND APPARATUS FOR GENERATING MEDICAL INFORMATION OF OBJECT

(71) Applicant: IRM INC., Seongnam-si (KR)

(72) Inventor: Seung Wook Choi, Seongnam-si (KR)

(73) Assignee: IRM INC., Seongnam-si (KR)

( * ) Notice: Subject to any disclaimer, the term of this patent is extended or adjusted under 35 U.S.C. 154(b) by 524 days.

(21) Appl. No.: 17/308,513

(22) Filed: May 5, 2021

(65) Prior Publication Data

US 2021/0257098 A1 Aug. 19, 2021

Related U.S. Application Data

(62) Division of application No. 15/111,830, filed as application No. PCT/KR2015/001851 on Feb. 26, 2015, now abandoned.

(30) Foreign Application Priority Data

| Mar. 10, 2014 | (KR) | ......................... 10-2014-0027953 |
| Aug. 22, 2014 | (KR) | ......................... 10-2014-0109953 |
| Aug. 22, 2014 | (KR) | ......................... 10-2014-0109954 |

(51) Int. Cl.
*G06F 16/00* (2019.01)
*G16H 50/20* (2018.01)
*G16H 10/60* (2018.01)

(52) U.S. Cl.
CPC ............. *G16H 50/20* (2018.01); *G16H 10/60* (2018.01)

(58) Field of Classification Search
CPC ...... G06F 21/64; G06F 16/951; H04W 12/06; H04W 12/02; H04L 63/083; H04L 63/0421; G16H 50/20; G16H 10/60
See application file for complete search history.

(56) References Cited

U.S. PATENT DOCUMENTS

| 9,042,617 B1 | 5/2015 | Reicher et al. |
| 9,251,295 B2 | 2/2016 | Adams et al. |

(Continued)

FOREIGN PATENT DOCUMENTS

| JP | 2001290890 A | 10/2001 |
| JP | 2002083058 A | 3/2002 |

(Continued)

OTHER PUBLICATIONS

Korean Office Action dated Mar. 25, 2016 for Application No. 10-2014-0109953.

(Continued)

*Primary Examiner* — Yicun Wu
(74) *Attorney, Agent, or Firm* — Studebaker & Brackett PC

(57) ABSTRACT

A method of generating information about a filter includes: setting at least one filter class corresponding to an operation for generating medical information of an object; setting at least one filter included in the filter class and configured to perform the operation; and setting at least one condition required to operate the filter. A method of generating medical information of an object includes: receiving at least one first content from at least one from among external apparatuses connected to a cloud; selecting a first filter that performs an operation based on the first content from among filters respectively included in a plurality of filter classes; and performing a preset operation by using the first filter.

6 Claims, 9 Drawing Sheets

(56) References Cited

U.S. PATENT DOCUMENTS

| | | |
|---|---|---|
| 9,639,615 B1 | 5/2017 | Veliah et al. |
| 2014/0279807 A1 | 9/2014 | Dimitrijevic |
| 2017/0041296 A1* | 2/2017 | Ford ................... G06F 21/64 |

FOREIGN PATENT DOCUMENTS

| | | |
|---|---|---|
| JP | 2004113730 A | 4/2004 |
| JP | 2010267042 A | 11/2010 |
| JP | 2012226632 A | 11/2012 |
| JP | 2014035703 A | 2/2014 |
| KR | 20110055921 A | 5/2011 |

OTHER PUBLICATIONS

Korean Office Action dated Jun. 20, 2016 for Application No. 10-2014-0109953.

International Search Report (PCT/ISA/210) dated Jun. 1, 2015, by the Korean Intellectual Property Office as the International Searching Authority for International Application No. PCT/KR2015/001851.

Written Opinion (PCT/ISA/237) dated Jun. 1, 2015, by the Korean Intellectual Property Office as the International Searching Authority for International Application No. PCT/KR2015/001851.

* cited by examiner

METHOD AND APPARATUS FOR GENERATING MEDICAL INFORMATION OF OBJECT

TECHNICAL FIELD

The present invention relates to a method and apparatus for generating medical information of an object, and in particular, to a method and apparatus for forming a filter that generates medical information of an object by performing a preset operation. Also, the present invention provides a method or apparatus for generating medical information of an object by using a workflow designed by using at least one filter that performs a preset operation.

BACKGROUND ART

Cloud computing refers to a computing environment based on the Internet or a network. A program infrastructure may be built in a data server on the Internet and users may use on demand, through computers or mobile phones, programs stored in the data server. In other words, users may use computing resources including intangible hardware and/or software, such as a cloud, through terminals or clients such as mobile phones.

As medical technology and communication technology have been developed, attempts have been actively made to converge the medical industry with the communication industry. In particular, a technology for generating desired tangible medical information by processing a diagnosis result of an object (e.g., a patient) and sharing the desired tangible medical information between persons in remote/distant places has been studied.

DETAILED DESCRIPTION OF THE INVENTION

Technical Problem

The present invention provides a method and apparatus for generating medical information of an object. Also, the present invention provides a computer-readable recording medium having embodied thereon a program for executing the method on a computer. Technical problems to be solved are not limited to the above technical problems, and there may be other technical problems.

Technical Solution

A method of generating information about a filter according to an aspect includes: setting at least one filter class corresponding to an operation for generating medical information of an object; setting at least one filter included in the filter class and configured to perform the operation; and setting at least one condition required to operate the filter.

A computer-readable recording medium according to another aspect has embodied thereon a program for executing the method on a computer.

An apparatus for generating information about a filter according to another aspect includes: a filter class setter configured to set at least one filter class corresponding to an operation for generating medical information of an object; a filter setter configured to set at least one filter included in the filter class and configured to perform the operation; and a filter condition setter configured to set at least one condition required to operate the filter.

A method of generating medical information of an object according to another aspect includes: receiving at least one first content from at least one from among external apparatuses connected to a cloud; selecting a first filter that performs an operation based on the first content from among filters respectively included in a plurality of filter classes; and performing a preset operation by using the first filter.

A computer-readable recording medium according to another aspect has embodied thereon a program for executing the method on a computer.

An apparatus included in a cloud system for generating medical information of an object according to another aspect includes: an interface unit configured to receive at least one first content from at least one from among external apparatuses connected to a cloud; and a filter selector configured to select a first filter that performs a preset operation based on the first content from among filters respectively included in a plurality of filter classes.

Advantageous Effects of the Invention

As described above, since a filter that performs a preset operation is formed, medical information of an object may be generated without a user's intervention. Also, since medical information of an object may be generated and provided based on an open platform, the medical information of the object may be provided without time and space constraints. Also, since a workflow is designed by using at least one filter that performs a preset operation, medical information of an object may be generated without a user's intervention.

MODE OF THE INVENTION

Embodiments of the present invention now will be described more fully hereinafter with reference to the accompanying drawings. The present invention may, however, be embodied in many different forms and should not be construed as limited to the embodiments set forth herein. Numerous modifications and adaptations will be readily apparent to one of ordinary skill in this art from the detailed description and the embodiments without departing from the scope of the present invention.

Figure 1:
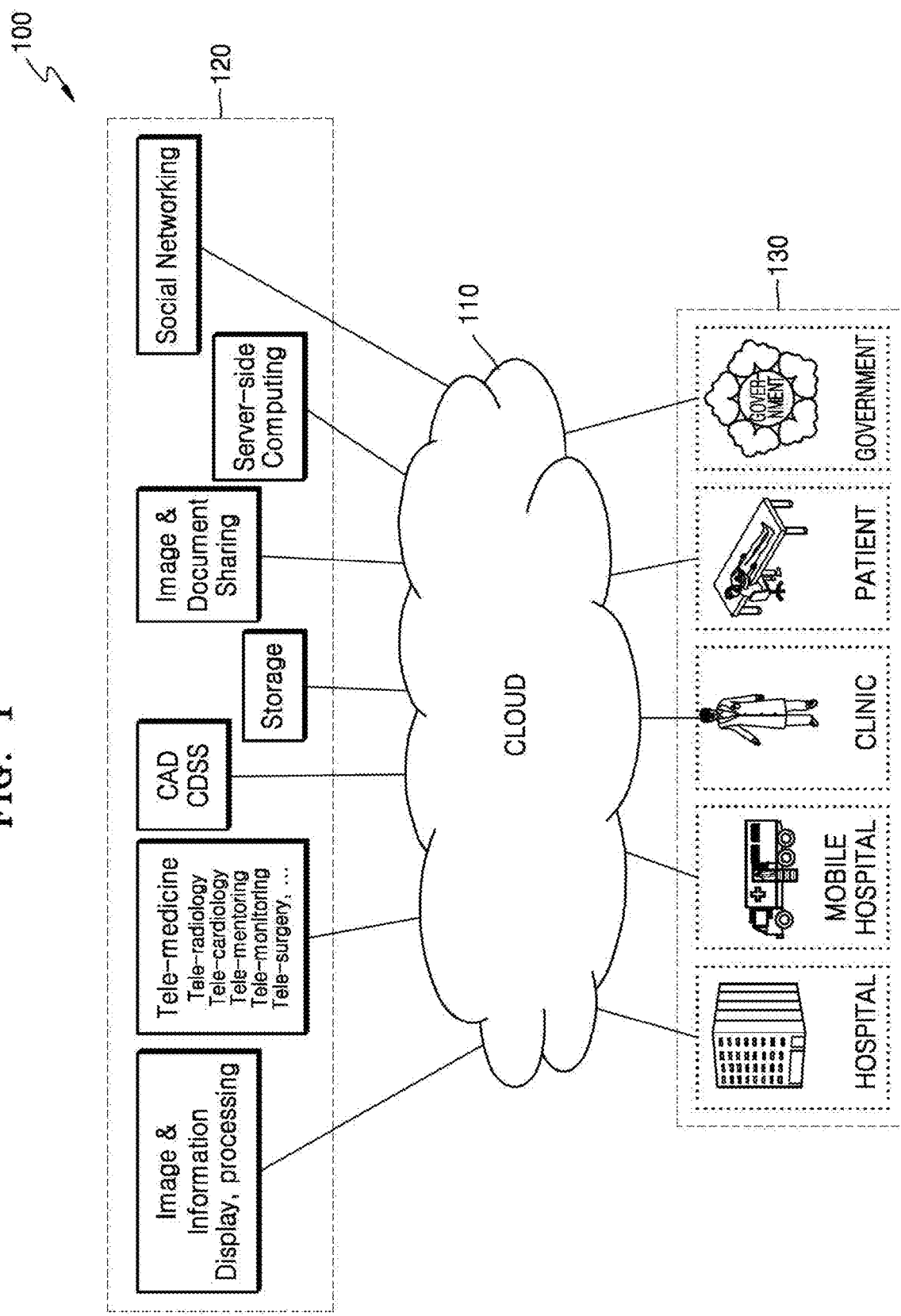
FIG. 1 is a conceptual diagram illustrating a system for providing medical information, according to an embodiment of the present invention.

FIG. 1 is a conceptual diagram illustrating a system 100 for providing medical information according to an embodiment of the present invention.

Referring to FIG. 1, the system 100 includes a cloud 110 and a user 130. Although the term 'user' is used for convenience of explanation in FIG. 1, the user 130 means an apparatus used by the user 130 and encompasses an external apparatus that may access the cloud 110. Also, the cloud 110 may be a predetermined server to which one or more external apparatus may make access through wired/wireless communication.

The system 100 according to an embodiment of the present invention refers to a system that generates medical information of an object based on the cloud 110 and provides the medical information to the user 130. The object may be, but not limited to, a patient who is required to be diagnosed.

In detail, the system 100 may generate medical information of an object based on an open platform and may provide the medical information to the user 130. For example, the system 100 includes a platform that provides various services 120 such as medical information search, storage, transmission, inquiry, or exchange based on the medical information standard such as Integrating the Healthcare Enterprise (IHE), Digital Imaging and Communications in Medicine (DICOM), or Health Level-7 (HL7) and the international standard such as Word Wide Web Consortium (W3C) or International Organization for Standardization (ISO).

For example, the services 120 provided by the system 100 may include a medical information providing or processing service, a tele-medicine service, a clinical decision supporting system service, a medical information storing or sharing service, a server-side computing service, and a social networking service. However, the services 120 are not limited to the above services, and may be any service provided by the system 100 according to an embodiment of the present invention as long as a work may be done by a user by using the medical information due to the service.

A system 200 for providing medical information will now be explained with reference to FIG. 2.

Figure 2:
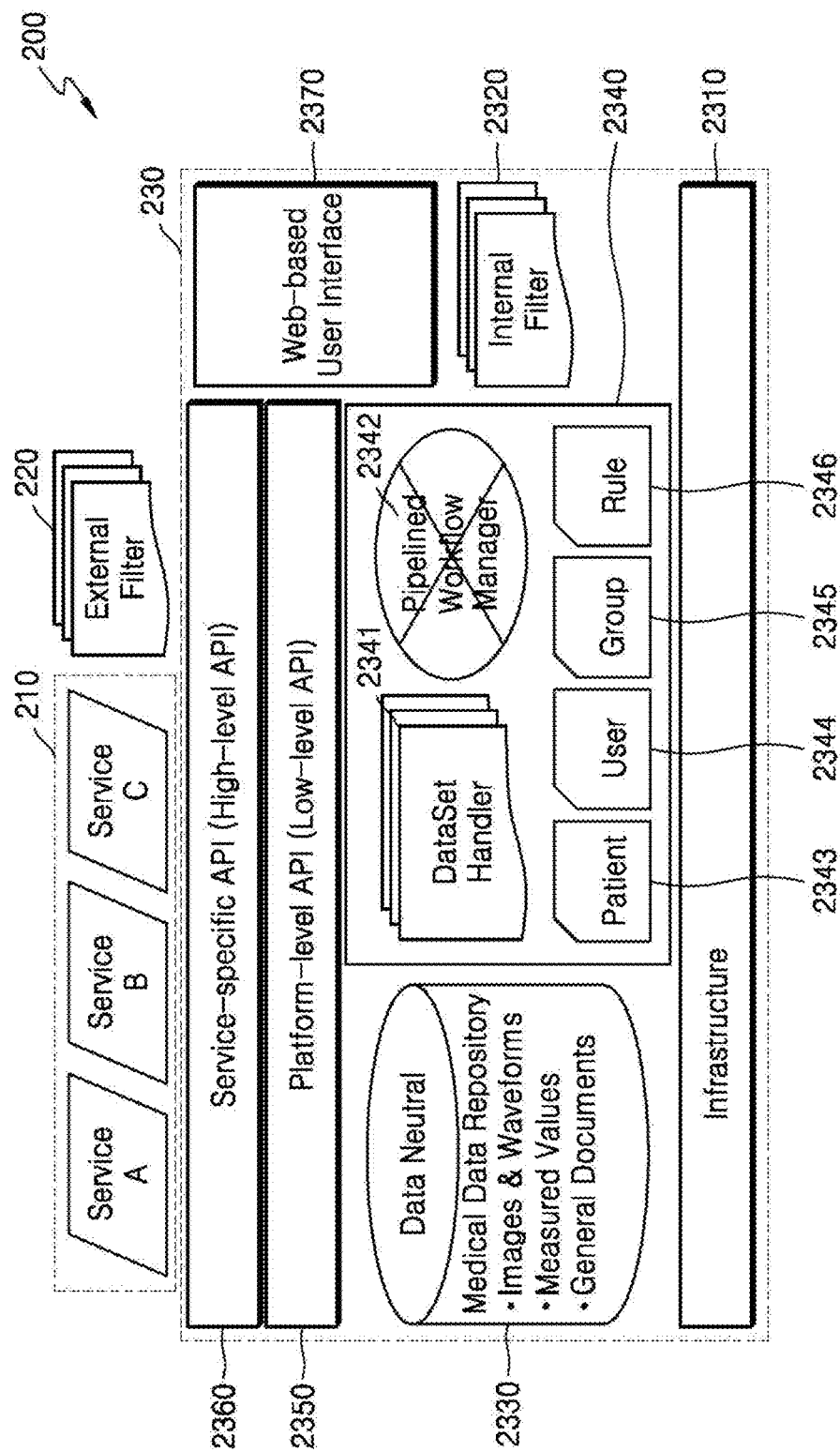
FIG. 2 is a diagram for explaining a system for providing medical information, according to an embodiment of the present invention.

FIG. 2 is a diagram for explaining the system 200 according to an embodiment of the present invention.

Services 210 provided by the system 200, an external filter 220, and an architecture 230 of a cloud are illustrated in FIG. 2. An infrastructure 2310, an internal filter 2320, a data storage 2330, a controller 2340, a platform-level application programming interface (API) 2350, a service-specific API 2360, and a user interface 2370 are included in the architecture 230. A dataset handler 2341, a workflow manager 2342, a patient manager 2343, a user manager 2344, a group manager 2345, and a condition manager 2346 are included in the controller 2340. Also, although not shown in FIG. 2, a filter manager is further included in the controller 2340.

Types of the services 210 are the same as those described with reference to FIG. 1. Accordingly, a detailed explanation of the types of the services 210 will not be given.

The external filter 220 refers to a filter that operates outside the cloud. In detail, the external filter 220 performs an operation outside a database of the cloud. For example, the external filter 220 may be included in at least one apparatus from among external apparatuses connected to the cloud. In this case, information about the external filter 220 may be generated, set, changed, and deleted by the filter manager of the architecture 230 and may be transmitted to the external apparatus, or may be generated, set, changed, and deleted by the external apparatus. The external filter 220 according to an embodiment of the present invention will be explained below in detail with reference to FIGS. 5 and 6.

The architecture 230 of FIG. 2 is an architecture that may be constructed in the cloud 110 of FIG. 1. Accordingly, it will be understood by one of ordinary skill in the art that general-purpose elements other than the elements illustrated in FIG. 2 may be further included.

Also, the infrastructure 2310, the data storage 2330, the controller 2340, the platform-level API 2350, the service-specific API 2360, and the user interface 2370 included in the architecture 230 of FIG. 2 may correspond to one or more processors. Each processor may be an array of logic gates, or a combination of a general-purpose microprocessor and a memory storing a program that may be executed by the microprocessor. Also, it will be understood by one of ordinary skill in the art that the processor may be another type of hardware.

The data storage 2330 stores and manages all types of content that may be processed by the cloud. The content used herein refers to any type of document including text, an image, or a video. In other words, examples of the content may include all types of documents, such as images, waveforms, and measured values, which may be processed by general arithmetic units. Accordingly, content and a document in an embodiment of the present invention are described as the same concept.

In the system 200 according to an embodiment of the present invention, one document may be included zero or more document sets DocSet. In other words, a document may not be included in a document set or may be included in one or more document sets. Also, a specific document has to belong to one group. The group used herein may refer to a group of a real organization such as a hospital or a department/division, or a virtual user set. The group will be explained below in detail. An ID for identifying each document is assigned in the cloud. An ID type related to a document and a definition thereof according to an embodiment of the present invention are shown in Table 1.

TABLE 1

| ID type | Definition |
| --- | --- |
| Document UID | Is a unique ID of a document, and is unique in a specific group that generates the document. |
| Document UUID | Is a unique ID separate from the Document UID, and is unique in all documents. For example, there is one Document UID for a first document whereas a Document UUID may vary whenever the first document is transmitted (or processed). |
| Filter UID | Is an ID indicating a filter that generates the document. |
| Patient Id | Is an ID indicating a patient related to the document. |

Each of all documents according to an embodiment of the present invention has a unique ID (UID), and the UID guarantees uniqueness only in a specific group. Also, each of all documents has a unique UUID separate from the UID and guarantees uniqueness in all of the documents. A document in the cloud according to an embodiment of the present invention corresponds to a document entry in an Integrating the Healthcare Enterprise (IRE) Cross Enterprise Document Sharing (XDS).

The dataset handler 2341 manages a document set. In detail, the dataset handler 2341 generates, sets, changes, and deletes a document set. The document set DocSet refers to a virtual set of real documents. Any processing in the cloud is performed in units of document sets. Also, a specific document set has to belong to one group. An ID for identifying each document set is assigned in the cloud. An ID type related to a document set and a definition thereof according to an embodiment of the present invention are shown in Table 2.

TABLE 2

| ID type | Definition |
| --- | --- |
| DocSet UID | Is a unique ID of a document set, and is unique in a specific group that generates the document set. |
| DocSet UUID | Is a unique ID separate from the document set UID, and is unique in all document sets. For example, there is one document set UID for a first document set whereas a document set UUID may vary whenever the first document set is transmitted (or processed). |
| DocSet Class UID | Indicates a type of a document set, and is used to designate an input/output method of a filter. |
| DocSet Group UID | Is used to express a relationship between document sets. |
| Filter UID | Indicates a filter that generates the document set. |
| Patient Id | Indicates a patient related to the document set. |

A document set in the cloud according to an embodiment of the present invention corresponds to a submission set in the IHE XDS.

Also, a document set has to have one document set class DocSet Class. The document set class used herein refers to a class of a document set. The document set class is used to designate an input/output method of a filter, and is expressed with a unique document set class UID that is unique in the cloud.

The workflow manager 2342 manages a workflow that operates in the cloud. In detail, the workflow manager 2342 generates, sets, changes, and deletes a workflow. A workflow according to an embodiment of the present invention will be explained below in detail with reference to FIG. 4.

The patient manager 2343 manages information about a patient. In detail, the patient manager 2342 generates, sets, changes, and deletes patient information. The patient refers to an owner of medical information or health information, and is different from a user that is another entity using the medical information. In reality, the patient receives different patient numbers according to organizations (e.g., hospitals or governments). Accordingly, the patient in the cloud may be expressed with different patient numbers in a plurality of groups and the linking of the different patient numbers may indicate the same patient.

The user manager 2344 manages information about a user. In detail, the user manager 2344 generates, sets, changes, and deletes user information. The term 'manage' used herein includes actions of generating, changing, and deleting patient information. The user refers to a user who uses services of the cloud and is different from the patient. For example, the user may be a medical staff member such as a doctor or a nurse, or may be a government official sometimes.

One user may belong to zero or more groups. In other words, the user may not belong to any group, or may belong to one or more groups. If the user belongs to one or more groups, the user may be given a group manager right. A right to search for and inquire about the afore-described document set may be given to an individual user. A user according to an embodiment of the present invention may be authenticated by a method of the system 200 itself or may be authenticated by a service provider that provides other authentication services.

The group manager 2345 manages information about a group. In detail, the group managers 2345 generates, sets, changes, and deletes group information. The group refers to a set of users. According to a configuration, the group may refer to a group of a real organization such as a hospital or a department/division, or a virtual user set.

The group may be an independent group or may be a group under one higher group. Also, the group may include a plurality of users. The group may give a manager right to manage the group to a specific user included in the group. In this case, the right to manage the group is inherited to sub-groups of the group. In other words, a manager of the specific group may also manage the sub-groups of the group.

A right to search for and inquire about a document set may be indirectly given through the group to which the user belongs. However, the right to search for and inquire about the document set is valid only in the designated group, and is not inherited to the sub-groups of the group.

The condition manager 2346 manages conditions set on the system 200. In detail, the condition manager 2346 generates, sets, changes, and deletes conditions. The conditions may correspond to a document set condition DocSet rule and/or a filter condition. The filter condition may be generated, set, changed, and deleted by the condition manager 2346, or may be generated, set, changed, and deleted by the filter manager.

In detail, the document set condition refers to a condition used to automatically give a right to search for and inquire about a specific document set to a user. Also, the filter condition refers to a condition used to automatically perform an operation of a filter. The internal filter 2320 or the external filter 220 may be included in the filter according to an embodiment of the present invention. In detail, the internal filter 2320 performs an operation in the database of the cloud. In this case, information about the internal filter 2320 is generated, set, changed, and deleted by the filter manager of the architecture 230.

A filter class, a filter condition, a filter queue, and a filter log related to the filter will now be explained in detail.

First, the filter class refers to a class of the filter, and an input/out method is expressed by using a document set class. One filter class may correspond to a plurality of filters. That is, there may be various filters having the same input/output method and function.

An input and an output of the filter may be expressed with zero or more document set classes. In detail, the filter may receive one document set and may output one document set, and may receive a plurality of documents sets and may generate a plurality of output document sets. Also, the filter may have an output function without having an input function or may have an input function without having an output function.

The internal filter 2320 refers to a filter that performs an operation in the database of the cloud, and may be a stored function of a database of the infrastructure 2310. The external filter 220 refers to a filter that performs an operation outside the database of the cloud and may operate by using the APIs 2350 and 2360 provided by the cloud.

The filter indicates an instance of the filter and indicates an actual instance of the filter expressed with a filter class. All filters having the same filter class UID may perform substantially the same function.

However, a default group and a default patient may be differently designated according to each filter. For example, the filter manger may automatically set a group of documents and a document set generated by the filter by designating a default group. Also, the filter manager may automatically set a patient of a document and a document set generated by the filter by designating a default patient.

The filter condition refers to at least one condition required to operate the filter. When the filter condition is satisfied, the filter automatically performs an operation. If a plurality of document sets are needed to operate the filter, a condition may be set according to each of the document sets.

For example, a time when the filter performs an operation may be designated as follows.

For example, an absolutely designed specific date and time (e.g., Apr. 5, 2014, 03:00 P.M.)

Alternatively, a predetermined period of time after the filter condition is satisfied (e.g., 5 hours after the filter condition is satisfied)

Alternatively, a predetermined period of time after the beginning (00:00 A.M.) of the day after the condition is satisfied (e.g., assuming that the condition is satisfied on Apr. 5, 2014, 03:00 P.M., 5 hours after Apr. 6, 2014, 00:00 A.M.)

When the filter condition is satisfied, the filter manager (or the condition manager 2346) registers the filter that is to perform an operation and necessary document sets in the filter queue and designates a time when the filter is to perform the operation. If the time when the filter is to perform the operation is not specified, the filter immediately performs the operation.

The filter queue refers to a wait queue for operating the filter. The internal filter 23320 processes content of the filter queue at a designated time interval (e.g., 60 seconds). The external filter 220 processes content of the filter queue according to filter procedure (FilterProc) module settings.

The filter log refers to a log about processing (action) of the internal filter 2320.

The internal filter 2320 and the external filter 220 according to an embodiment of the present invention will be explained below in detail with reference to FIGS. 5 through 6.

The user interface 2370 refers to a user interface for managing the cloud and searching for and inquiring about information. For example, the user interface 2370 may be a web-based interface.

The platform-level API 2350 refers to an API collection for directly interfacing between the cloud and external apparatuses. Also, the service-level API 2360 refers to an API collection based on the platform-level API 2350 for a specific service (e.g., a service A) from among the services 210 provided by the system 200.

The infrastructure 2310 refers to an infrastructure for providing all of the afore-described services of the cloud. For example, the infrastructure 2310 may correspond to, but not limited to an Amazon Web Services cloud service.

The cloud having the architecture 230 may generate and provide medical information of an object (e.g., a patient) based on an open platform, and may provide the medical information of the object to a user without time and space constraints.

Figure 3:
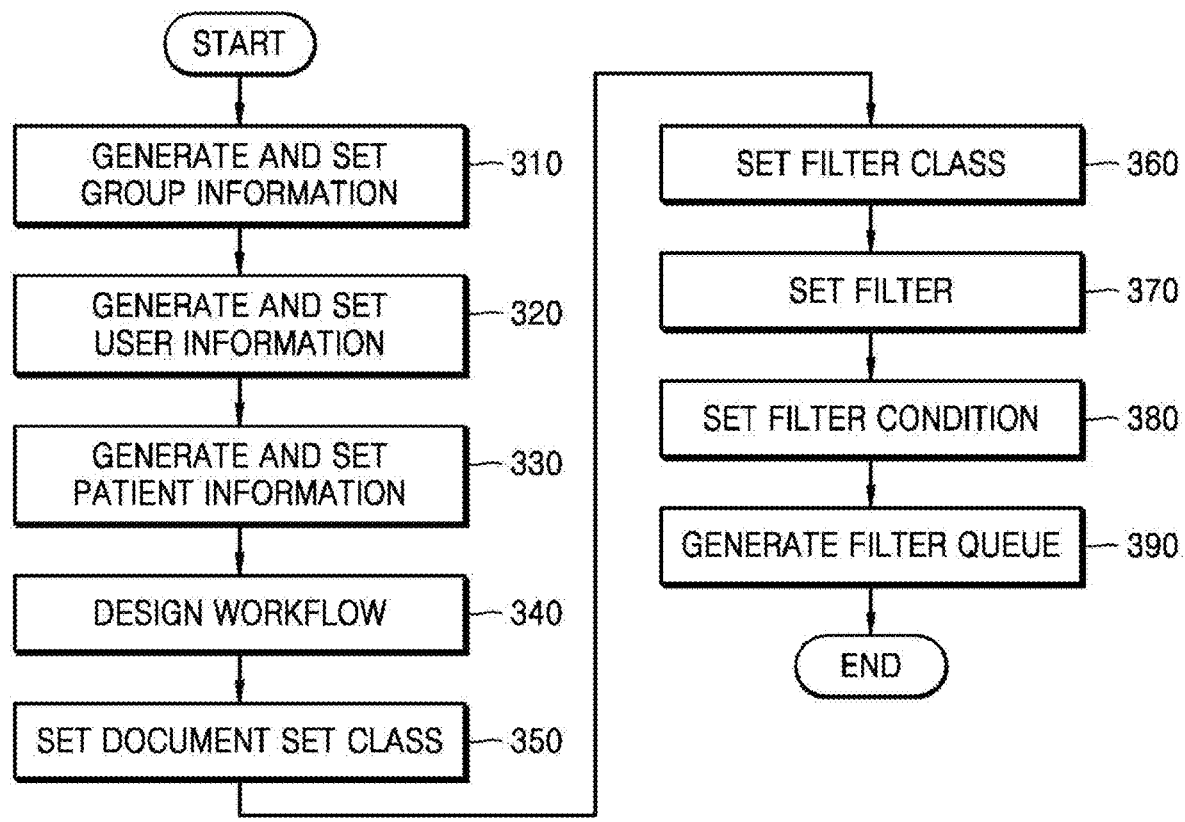
FIG. 3 is a flowchart for explaining an operation of a system for providing medical information, according to an embodiment of the present invention.

FIG. 3 is a flowchart for explaining an operation of a system for providing medical information (referred to as the medical information providing system) according to an embodiment of the present invention.

Referring to FIG. 3, an operation of the medical information providing system includes steps that are sequentially performed by the system 100 or 200 or the cloud 110 of FIGS. 1 and 2. Accordingly, although omitted, the description of the medical information providing system or the cloud 110 of FIGS. 1 and 2 may apply to the operation of the medical information providing system of FIG. 3.

For convenience of explanation, it is assumed that each of the steps of FIG. 3 is performed by the 'cloud 110'. However, it will be understood by one of ordinary skill in the art that an entity that performs each of the steps of FIG. 3 may be any of the elements included in the architecture 230 of FIG. 2.

In step 310, the cloud 110 generates and sets group information.

First, the cloud 110 generates a group (hereinafter, referred to as a master group) that represents an organization that is to open a service, based on an external signal input from a user. Organizations such as real hospitals may be generated under the master group. For example, the cloud 110 may generate a group as shown in Table 3.

TABLE 3

Group hierarchy

| Group: Radionet | top group: master group |
| Group: SNUH | primary child group: medical institution |
| Group: Radiology | secondary child group: department in medical institution |
| Group: CMC | primary child group: medical institution |
| Group: Cardiology | secondary child group: department in medical institution |
| Group: GuroClinic | primary child group: medical institution |

Referring to Table 3, the cloud 110 may generate a master group Rradionet, and may generate real medical institutions such as Seoul National University Hospital (SNUH), Catholic Medical Center (CMC), and Guro Clinic as child groups under the master group Radionet. Also, after forming the real medical institutions as groups, the cloud 110 may register departments in the medical institutions as other child groups Radiology and Cardiology.

A database table structure for storing group information is shown in Table 4.

TABLE 4

Table "VGroup"

| Column | Type | Modifiers | |
| --- | --- | --- | --- |
| vgroup_key | integer | not null | PK |
| vgroup_id | character varying(64) | not null | UK |
| vgroup_id_type | character varying(16) | not null | UK |
| vgroup_name | character varying(256) | | |
| vgroup_type | character varying(64) | | |
| parent_vgroup_key | integer | | FK |
| created_dttm | timestamp without time zone | not null | |
| deleted_dttm | timestamp without time zone | | |

A detailed description of attributes included in the table structure of Table 4 is shown in Table 5.

TABLE 5

| Attribute | Description |
|---|---|
| Group Id | Indicates an ID of a group, and sets assigning_authority_id that is one of three elements constituting a patient number to Group Id. It may be expressed by using, but not limited to, ISO OID. For example, when a medial institution code such as 82999 is given, it indicates a 999$^{th}$ hospital in Korea (82). |
| Group Id Type | Indicates a type of the ID of the group, and sets assigning_authority_id_type that is one of three elements constituting the patient number to Group Id Type. When a group ID is registered by using ISO OID, ISO has to be designated. However, otherwise, self-determination may be used. For example, Group Id Type may be set to "BIS-CLOUD". |
| Group Name | Indicates a name of the group that may be recognized by a person. For example, it may be set to an official name of a medical institution. |
| Group Type | Indicates an item for indicating a type of the group. For example, a hospital may be set to "HOSPITAL", and a clinic may be set to "CLINIC". |
| Parent Group | Indicates a parent group. |

In step 320, the cloud 110 generates and sets user information.

The cloud 110 generates a user (hereinafter, referred to as a master manager) who is to manage the master group, based on an external signal input from the user. The cloud 110 gives a right to manage the master group to the master manager. In the medical information providing system according to an embodiment of the present invention, when one user has a right to manager a certain group (that is, is a group manager), the user may manage sub-groups of the group. Accordingly, when the master manager has a right to manage a master group, it means that the master manager may generate a plurality of groups under the master group. Only a group manager may add a user or a patient to the group or child groups of the group.

For example, an example where a group manager is set according to a group is shown in Table 6.

TABLE 6

| Group hierarchy | group manager |
|---|---|
| Group: Radionet | bioadmin |
| Group: SNUH | bioadmin, snuhadmin |
| Group: Radiology | bioadmin, snuhadmin, snuhradioadmin |
| Group: CMC | bioadmin, cmcadmin |
| Group: Cardiology | bioadmin, cmcadmin |
| Group: GuroClinic | bioadmin, gurocadmin |

Referring to Table 6, a master manager bioadmin may manage both a group Radionet and child groups. A group manager snuhadmin may manage a group SNUH and a group Radiology that is a child group of the group SNUH. If a separate manager is necessary for the group Radiology, a group manager snuhradioadmin may be additionally designated as shown in Table 6.

A user in the medical information providing system according to an embodiment of the present invention may belong to a plurality of groups. In this case, when the user belongs to a specific group and is given a management right, the user becomes a manger of the group and, otherwise, becomes a general user. After a group manager is generated, the cloud 110 generates as many general users as needed and makes the general users belong to groups.

However, an inquiry right, unlike a management right that is inherited, is not inherited. That is, when a user is to inquire about a document of a group, the user has to belong to the group. For example, referring to Table 6, the group manager snuhadmin may manage the group SNUH and the group Radiology, but may not inquire about a document of the group Radiology. In order for the user snuhadmin to inquire about the document of the group Radiology, the user snuhadmin has to belong to the group Radiology.

The user may have a plurality of authentication methods. For example, the user may log on through self authentication of the medical information providing system, or may log on by using other authentication accounts (e.g., a Google account).

A database table structure for storing user information is shown in Table 7.

TABLE 7

Table "Users"

| Column | Type | Modifiers | |
|---|---|---|---|
| user_key | integer | not null | PK |
| user_name | character varying(256) | not null | |
| created_dttm | timestamp without time zone | not null | |
| deleted_dttm | timestamp without time zone | | |

A database table structure for setting a relationship between a group and a user is shown in Table 8.

TABLE 8

Table "VGroupUser"

| Column | Type | Modifiers | |
|---|---|---|---|
| vgroup_user_key | integer | not null | PK |
| vgroup_key | integer | not null | FK |
| user_key | integer | not null | FK |
| admin_role | Boolean | default false | |

In step 330, the cloud 110 generates and sets patient information.

The cloud 110 may generate and set patient information, based on an external signal input from the user. In the medical information providing system according to an embodiment of the present invention, a patient may have attributes such as a patient number, a name, a sex, and a birthdate. From among the attributes, the patient number includes three parts patient_id_value, assigning_authority_id, and assigning_authority_id type. In this case, the parts assigning_authority_id and assigning_authority_id type correspond to the attributes Group Id and Group Id Type of the group, and patient_id_value indicates the patient number of the group. Accordingly, the patient in the medical information providing system according to an embodiment of the present invention belongs to only one group.

A database table structure for storing the patient information is shown in Table 9.

TABLE 9

Table "Patient"

| Column | Type | Modifiers | |
|---|---|---|---|
| patient_key | integer | not null | PK |
| vgroup_key | integer | not null | FK |
| patient_id_value | character varying(64) | not null | |

TABLE 9-continued

Table "Patient"

| Column | Type | Modifiers |
|---|---|---|
| patient_name | character varying(256) | not null |
| patient_sex | character varying(1) | |
| patient_birth_dttm | timestamp without time zone | |
| related_patient_key | integer | FK |
| created_dttm | timestamp without time zone | not null |
| deleted_dttm | timestamp without time zone | |

A detailed description of attributes included in the table structure of Table 9 is shown in Table 10.

TABLE 10

| Attribute | Description |
|---|---|
| Patient Id Value | Indicates patient_id_value that is a first part from among three parts of a patient number. |
| Patient Name | Indicates a name of a patient. For example, it may be input by using a HL7 method (Last name^First name^Middle name^Suffix^Prefix). |
| Patient Sex | Indicates a patient sex. For example, it may be input as 'M = male, F = female, O = other, or U = unknown'. |
| Patient Birthdate | Indicates a birthdate of the patient. |
| Related Patient | Indicates connection with other patient information. |

Even the same patient may go to a plurality of medical institutions. In this case, different patient numbers may be assigned to the same patient according to medical institutions. Accordingly, the medical information providing system according to an embodiment of the present invention generates a patient according to each medical institution. However, patient attributes in the medical information providing system include an attribute Related Patient as shown in Table 10, and thus other patient information may be connected. In other words, the cloud 110 may find and connect pieces of information about the same patient distributed in medical institutions by using the attribute Related Patient.

In step 340, the cloud 110 designs a workflow based on an external signal input from a manager of the cloud 110.

The workflow is the flow of an operation performed by at least one filter. The medical information providing system according to an embodiment of the present invention generates medical information of an object (e.g., a patient) according to the workflow, and provides the medical information to a user. A workflow will now be explained with reference to FIG. 4.

Figure 4:
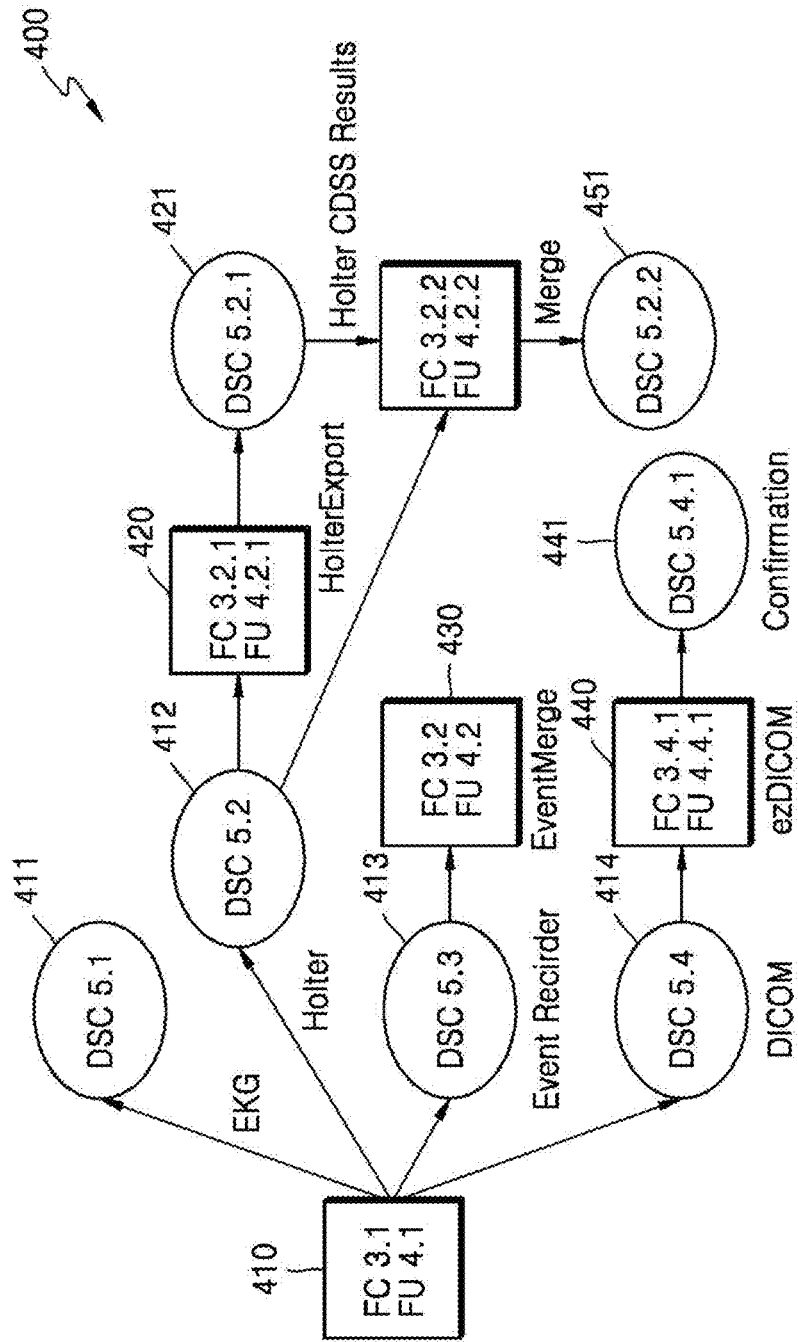
FIG. 4 is a view illustrating a workflow according to an embodiment of the present invention.

FIG. 4 is a view illustrating a workflow 400 according to an embodiment of the present invention.

The workflow 400 designed by the cloud 110 is illustrated in FIG. 4. Although the workflow 400 is illustrated in FIG. 4 for convenience of explanation, the workflow 400 designed by the cloud 110 is not limited to that of FIG. 4. In other words, any workflow in which medical information of an object (e.g., a patient) may be generated by using at least one filter belonging to at least one filter set or a single filter set and may be provided to a user may be included in the scope of the present invention without limitations.

A circular portion in the workflow 400 of FIG. 4 refers to a document set class DSC. At least one document may be included in one document set. Accordingly, it will be understood by one of ordinary skill in the art that although a specific document set class is described in each circular portion of FIG. 4, the same applies to another document belonging to the document set. The document set class, the document set, and the document are the same as those described with reference to FIG. 2, and thus a detailed explanation thereof will not be given.

Also, a rectangular portion in the workflow 400 of FIG. 4 refers to a filter class FC and a filter FU included in the filter class. At least one filter may be included in one filter class. Accordingly, it will be understood by one of ordinary skill in the art that although a specific filter class and a filter are described in each rectangular portion of FIG. 4, the same applies to another filter included in the filter class. The filter class and the filter are the same as those described with reference to FIG. 2, and thus a detailed explanation thereof will not be given.

Also, detailed names of the document set class, the filter class, and the filter of FIG. 4 are added for convenience, and thus the present invention is not limited thereto.

A filter 4.1 410 that is one instance of a filter class 3.1 generates one or more from among four document sets EKG 411, Holter 412, Event Recorder 413, and DICOM 414. The filter 4.1 410 may be an external filter that generates a document set, or may be an internal filter that generates a document set by using a signal received from an external apparatus. The document set EKG 411 expressed with a document set class 5.1 may be stored in the data storage 2330.

A filter 4.2.1 420 that is one instance of a filter class 3.2.1 receives the document set Holter (document set class 5.2) 412 and outputs a document set Clinical Decision Supporting System (CDSS) Results (a document set class 5.2.1) 421.

A filter 4.2.2 450 that is one instance of a filter class 3.2.2 generates a new document set (a document set class 5.2.2) 451 by combining the document set Holter 412 with the document set CDSS Results 421.

A filter 4.2 430 that is one instance of a filter class 3.2 combines the document set Event Recorder 413 that is expressed with a document set class 5.3.

A filter 4.4.1 440 that is one instance of a filter class 3.4.1 provides the document set DICOM 414 that is expressed with a document set class 5.4 to an external apparatus. The external apparatus displays the document set DICOM 414 on a screen. The displayed document set 441 may be checked by the cloud 110.

Referring back to FIG. 3, in step 350, the cloud 110 sets a document set class. In other words, the cloud 110 sets a document set class that is needed to operate the workflow 400 that is designed in step 340.

The cloud 110 assigns a UID to each document set and a filter and sets the UID in the medical information providing system. For example, the filter class 3.1 410 and the document set class 5.1 411 of FIG. 4 may be respectively expressed with UIDs such 1.2.410.200054.3.1 and 1.2.410.200054.5.1. The setting of the document set class is completed when the UID and a name of the document set class are designated.

A database table structure for storing document set class information is shown in Table 11.

TABLE 11

Table "DocSetClass"

| Column | Type | Modifiers |
|---|---|---|
| docset_class_uid | character varying(64) | not null PK |
| docset_class_type | character varying(10) | not null |
| docset_class_name | character varying(256) | not null |

A detailed description of attributes included in the table structure of Table 11 is shown in Table 12.

TABLE 12

| Attribute | Description |
|---|---|
| DocSet Class UID | Indicates a UID of a document set class, and a unique UID is assigned to each document set class. |
| DocSet Class Type | Indicates a type of the document set class and is used only for reference. |
| DocSet Class Name | Indicates a name of the document set class. |

In step 360, the cloud 110 sets a filter class. In other words, the cloud 110 sets a filter class that is needed to operate the workflow 400 designed in step 340.

In order for the cloud 110 to set the filter class, several additional attributes are further necessary in addition to a filter class UID and a filter class name.

A database table structure for storing filter class information is shown in Table 13 and Table 14.

TABLE 13

Table "FilterClass"

| Column | Type | Modifiers |
|---|---|---|
| filter_class_uid | character varying(64) | not null PK |
| filter_class_name | character varying(256) | not null |
| filter_type | character varying(10) | not null |

TABLE 13-continued

Table "FilterClass"

| Column | Type | Modifiers |
|---|---|---|
| filter_proc_name | character varying(256) | |
| filter_proc_args | character varying(256) | |

TABLE 4

Table "FilterInOut"

| Column | Type | Modifiers |
|---|---|---|
| filter_class_uid | character varying(64) | not null PK, FK |
| docset_type | character varying(1) | not null PK |
| docset_class_uid | character varying(64) | not null PK, FK |

A detailed description of attributes included in the table structure of Table 13 and Table 14 is shown in Table 15.

TABLE 15

| Attribute | Description |
|---|---|
| Filter Class UID | Is a UID of a filter class, and a unique UID is assigned to each filter class. |
| Filter Class Name | Indicates a name of the filter class. |
| Filter Class Type | Indicates a type of the filter class and indicates an internal filter I or an external filter E. |
| Filter Proc Name | Is set only in the internal filter and is a name of a database procedure. |
| Filter Proc Args | Is set in the internal filter and is factors of the database procedure. |
| DocSet Type | Indicates whether a designated document set is an input I or an output O of a filter. |
| DocSet Class UID | Designates an input or output document set of the filter. |

Also, the cloud 110 sets an input document set and an output document set that may be processed by each filter class.

For example, the cloud 110 may set a filter class as shown in Table 16.

TABLE 16

| filter_class_uid | filter_class_name docset_type | type | filter_proc_name docset_class_uid |
|---|---|---|---|
| 1.2.410.200054.3.1 | data uploader | E | |
| | O | | 1.2.410.200054.5.1 |
| | O | | 1.2.410.200054.5.2 |
| | O | | 1.2.410.200054.5.3 |
| | O | | 1.2.410.200054.5.4 |
| 1.2.410.200054.3.2 | Holter data creator | E | |
| | I | | 1.2.410.200054.5.3 |
| 1.2.410.200054.3.2.1 | CDSS caller | E | |
| | I | | 1.2.410.200054.5.2 |
| | O | | 1.2.410.200054.5.2.1 |
| 1.2.410.200054.3.2.2 | data merger | I | FilterQueue_bypass |
| | I | | 1.2.410.200054.5.2 |
| | I | | 1.2.410.200054.5.2.1 |
| | O | | 1.2.410.200054.5.2.2 |
| 1.2.410.200054.3.4.1 | DICOM viewer | E | |
| | I | | 1.2.410.200054.5.4 |
| | O | | 1.2.410.200054.5.4.1 |

In step 370, the cloud 110 sets a filter. In other words, the cloud 110 sets a filter that is needed to operate the workflow 400 designed in step 340.

A database table structure for storing filter information is shown in Table 17.

TABLE 17

Table "Filter"

| Column | Type | Modifiers | |
|---|---|---|---|
| filter_key | integer | not null | PK |
| filter_uid | character varying(64) | not null | UK |
| filter_class_uid | character varying(64) | not null | FK |
| filter_name | character varying(256) | not null | |
| filter_proc_args | character varying(32) | | |
| default_vgroup_key | integer | | FK |
| default_patient_key | integer | | FK |
| user_key | integer | | FK |
| created_dttm | timestamp without time zone | not null | |
| deleted_dttm | timestamp without time zone | | |

A detailed description of attributes included in the table structure of Table 17 is shown in Table 18.

TABLE 18

| Attribute | Description |
|---|---|
| Filter UID | Indicates a UID of a filter and is a unique value for each filter. |
| Filter Class UID | Indicates a type of the filter and sets a filter class UID. |
| Filter Name | Indicates a filter name. |
| Filter Proc Args | Re-defines factors of a database procedure that is used in an internal filter. |
| Default Group | Indicates a group that is automatically set when there is no group information in a document set processed by the filter. |
| Default Patient | Indicates a patient that is automatically set when there is no patient information in the document se processed by the filter. |

For example, the cloud 110 may set a filter as shown in Table 19.

TABLE 19

| filter_uid | filter_class_uid | filter_name |
|---|---|---|
| 1.2.410.200054.4.1.2.152.82.177.100.84.74.1598 | 1.2.410.200054.3.1 | Bioroid02(ejoonie) |
| 1.2.410.200054.4.1.2.152.82.177.100.84.74.1582 | 1.2.410.200054.3.1 | Bioroid |
| 1.2.410.200054.4.1.2.20.137.253.246.167.124.1347 | 1.2.410.200054.3.1 | Bioroid |
| 1.2.410.200054.4.1.2.152.82.177.100.84.74.2289 | 1.2.410.200054.3.1 | Bioroid |
| 1.2.410.200054.4.1.2.20.137.253.246.167.124 | 1.2.410.200054.3.1 | Bioroid |
| 1.2.410.200054.4.1 | 1.2.410.200054.3.1 | BioPump |
| 1.2.410.200054.4.1.2.152.82.177.100.84.74 | 1.2.410.200054.3.1 | Bioroid (ejoonie) |
| 1.2.410.200054.4.1.2.12.223.164.47.47.236 | 1.2.410.200054.3.1 | Bioroid |
| 1.2.410.200054.4.1.2.8.212.43.25.38.81 | 1.2.410.200054.3.1 | Bioroid |
| 1.2.410.200054.4.2 | 1.2.410.200054.3.2 | EventMerge |
| 1.2.410.200054.4.2.1 | 1.2.410.200054.3.2.1 | HolterExport |
| 1.2.410.200054.4.2.2 | 1.2.410.200054.3.2.2 | SimpleMerge |
| 1.2.410.200054.4.4.1 | 1.2.410.200054.3.4.1 | ezDICOM |

In step 380, the cloud 110 sets a filter condition.

If the cloud 110 does not set a filter condition, document sets may be simply stored but the workflow 400 of FIG. 4 may not be obtained. The filter condition includes i) setting of a filter that is to perform an operation and ii) setting of an input condition for performing the operation of the filter.

First, when the input condition of the filter is satisfied, a database table structure for storing information of the operation to be performed by the filter is shown in Table 20.

TABLE 20

Table "FilterRule"

| Column | Type | Modifiers |
|---|---|---|
| filter_rule_key | integer | not null PK |
| filter_key | integer | not null FK |
| filter_rule_name | character varying(256) | |
| scheduled_dttm | timestamp without time zone | |
| scheduled_delay | integer | |
| created_dttm | timestamp without time zone | not null |
| deleted_dttm | timestamp without time zone | |

A detailed description of attributes included in the table structure of Table 20 is shown in Table 21.

TABLE 21

| Attribute | Description |
|---|---|
| Filter Rule Name | Indicates a name of a filter rule. |
| Filter | Selects a filter that is to perform an operation. |
| Scheduled Time | Designates an absolute time when the filter is to perform the operation, and the filter performs the operation on the designed time. The designating of the absolute time is performed before a relative time is designated. |
| Scheduled Delay | Designates the relative time when the filter is to perform the operation, and the filter performs the operation a designated period of time after a current time in a a) mode, or, a designated period of time after tomorrow 00:00 A.M. in a b) mode. For example, assuming that a current time is Feb. 5, 2014, 18:00 and an attribute Scheduled Delay is 3:00, the filter performs the operation on Feb. 5, 2014, 21:00 in the a) mode and the filter performs the operation on February 6, 2014, 3:00 in the b) mode. |

Next, a database table structure for setting the input condition of the filter is shown in Table 22.

TABLE 22

Table "FilterRuleInput"

| Column | Type | Modifiers |
|---|---|---|
| filter_rule_input_key | integer | not null PK |
| filter_rule_key | integer | not null FK, UK |
| docset_class_uid | character varying(64) | not null FK, UK |

TABLE 22-continued

Table "FilterRuleInput"

| Column | Type | Modifiers |
|---|---|---|
| filter_key | integer | FK, UK |
| vgroup_key | integer | FK, UK |
| patient_key | integer | FK, UK |

A detailed description of attributes included in the table structure of Table 22 is shown in Table 23.

TABLE 23

| Attribute | Description |
|---|---|
| Filter Rule | Selects a filter condition. |
| DocSet Class UID | Sets which document set is to be prepared to perform an operation of a filter. |
| Filter | Sets which filter is to generate the document set. |
| Group | Sets which group the document set is to belong to. |
| Patient | Sets which patient is to own the document set. |

Referring to the workflow 400 of FIG. 4, the workflow is needed to be set only for the document set Holter 412 and the document set DICOM 414. This may be obtained when the cloud 110 sets as shown in Table 24.

TABLE 24

| filter_rule_name | filter_uid docset_class_uid | filter | scheduled_dttm vgroup | delay patient |
|---|---|---|---|---|
| HolterExport rule | 1.2.410.200054.4.2.1 1.2.410.200054.5.2 | | | |
| Merger rule | 1.2.410.200054.4.2.2 1.2.410.200054.5.2 1.2.410.200054.5.2.1 | | | |
| ezDICOM rule | 1.2.410.200054.4.4.1 1.2.410.200054.5.4 | | | |

When a new document set is generated, a function FilterRule_apply( ) is automatically called. In this case, the cloud 110 searches for a filter condition to determine whether there is a filter to be applied to the new document set and records a result on a filter queue. If an input condition of the filter condition includes only one document set, the filter condition is used as soon as the document set satisfying the condition is generated. However, when the input condition of the filter condition includes a plurality of document sets (that is, when the filter has to process a plurality of documents sets at one time), the filter condition is used when all of the document sets needed to perform an operation of the filter are prepared.

Content of Table 24 will now be explained as follows.

1) According to a filter condition "HolterExport rule", a filter 1.2.410.200054.4.2.1 performs an operation as soon as a document set for a document set class 1.2.410.200054.5.2 is prepared.

2) According to a filter condition "Merger rule", a filter 1.2.410.200054.5.2.2 performs an operation when all document sets for document set classes 1.2.410.200054.5.2 and 1.2.410.200054.5.2.1 are prepared.

3) According to a filter condition "ezDICOM rule", a filter 1.2.410.200054.4.4.1 performs an operation when a document set for a document set class 1.2.410.200054.5.4 is prepared.

In step 390, a filter queue is generated. The filter queue is not set but is generated as a result of using the filter condition, and stores pieces of information about the filter that is to perform an operation and a result of the operation of the filter.

The filter queue includes i) storing of information about the filter that is to perform an operation and ii) storing of information about a document set that is to be input to the filter.

First, a database table structure for storing information about a filter that is to perform an operation is shown in Table 25.

TABLE 25

Table "FilterQueue"

| Column | Type | Modifiers |
|---|---|---|
| filter_queue_key | integer | not null PK |
| filter_queue_uuid | uuid | not null UK |
| filter_key | integer | not null FK |
| filter_result_text | text | |
| filter_result_code | integer | |
| scheduled_dttm | timestamp without time zone | |
| performed_dttm | timestamp without time zone | |
| created_dttm | timestamp without time zone | not null |

A detailed description of attributes included in the table structure of Table 25 is shown in Table 26.

TABLE 26

| Attribute | Description |
|---|---|
| Filter Queue UUID | Is a UUID of a filter queue, and is used to process a filter operation by using an XDS method. |
| Filter | Designates a filter that is to perform an operation. |
| Filter Result Text | Indicates a result of the operation of the filter. |
| Filter Result Code | Indicates a result code of the operation of the filter. |
| Scheduled Time | Indicates a time when the filter is to perform the operation. |
| Performed Time | Indicates a time when the filter performs the operation. |

Next, a database table structure for storing information about a document set that is to be input to a filter is shown in Table 27.

TABLE 27

Table "FilterQueueInput"

| Column | Type | Modifiers |
|---|---|---|
| filter_queue_input_key | integer | not null PK |
| filter_queue_input_uuid | uuid | not null UK |
| filter_queue_key | integer | not null UK2 |
| docset_key | integer | not null UK2 |
| created_dttm | timestamp without time zone | not null |

A detailed description of attributes included in the table structure of Table 27 is shown in Table 28.

TABLE 28

| Attribute | Description |
|---|---|
| Filter Queue Input UUID | Is a UUID of a filter queue input, and is used to process a filter operation by using an XDS method. |
| Filter Queue | Designates a filter queue. |
| DocSet | Designates a document set. |

As described above, when pieces of information about a filter that is to perform an operation is stored in a filter queue, the filter performs the operation as follows according to a type of the filter.

1) An internal filter to perform an operation according to a database job manager. The database operation manager periodically calls a function FilterQueue_execute( ). The function is used to find the internal filter in content of the filter queue and then the database operation manager enables the internal filter to perform an operation at a time when the filter has to perform the operation.

2) An external filter performs an operation according to a program FilterProc. The program FilterProc used herein refers to an interface module for realizing an external filter. An external filter will be explained below in detail with reference to FIG. 6.

Figure 5:
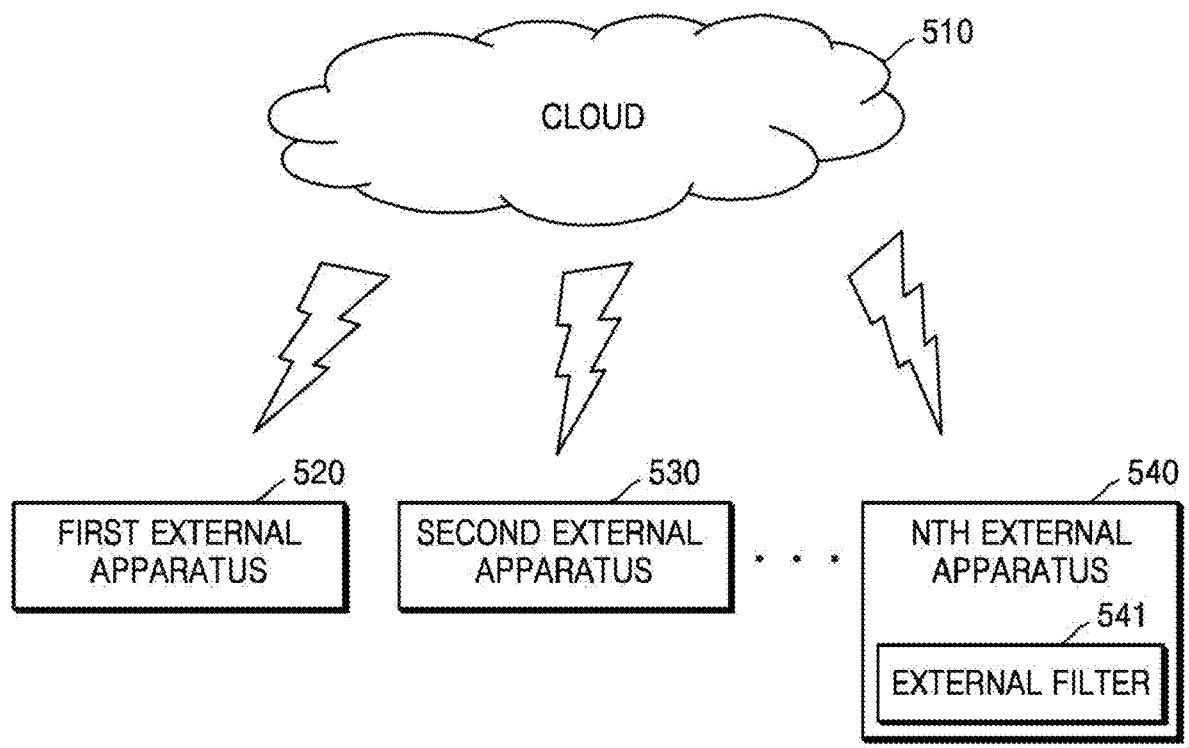
FIG. 5 is a diagram for explaining an external filter, according to an embodiment of the present invention.

FIG. 5 is a diagram for explaining an external filter 541 according to an embodiment of the present invention.

A cloud 510 and external apparatuses 520, 530, and 540 connected to the cloud 510 are illustrated in FIG. 5. In this case, the cloud 510 and the external apparatuses 520, 530, and 540 may be connected to each other through wired or wireless communication. For example, the cloud 510 and the external apparatuses 520, 530, and 540 may be connected through, but not limited to, an IHE XDS or Mobile-access to Health Document (MHD) standard protocol. A communication protocol through which the cloud 510 and the external apparatuses 520, 530, and 540 are connected to each other will be explained below with reference to FIG. 6.

An external apparatus may be any apparatus as long as it may communicate with another external apparatus or the cloud 510. For example, each of the external apparatuses 520, 530, and 540 may correspond to, but not limited to, medical equipment, a PC, or a mobile terminal for obtaining diagnostic information of a patient.

The external filter 541 may be included in at least one of the external apparatuses 520, 530, and 540. In this case, the external filter 541 and the cloud 510 may transmit/receive an operation through a program FilterProc. The program FilterProc searches for filter operations to be processed by the program FilterProc by using a designated filter UID, downloads input document sets, performs filter processing, configures generated resultant documents into a new document set, and uploads the new document set. Setting of the program FilterProc will be explained with reference to FIG. 6.

Figure 6:
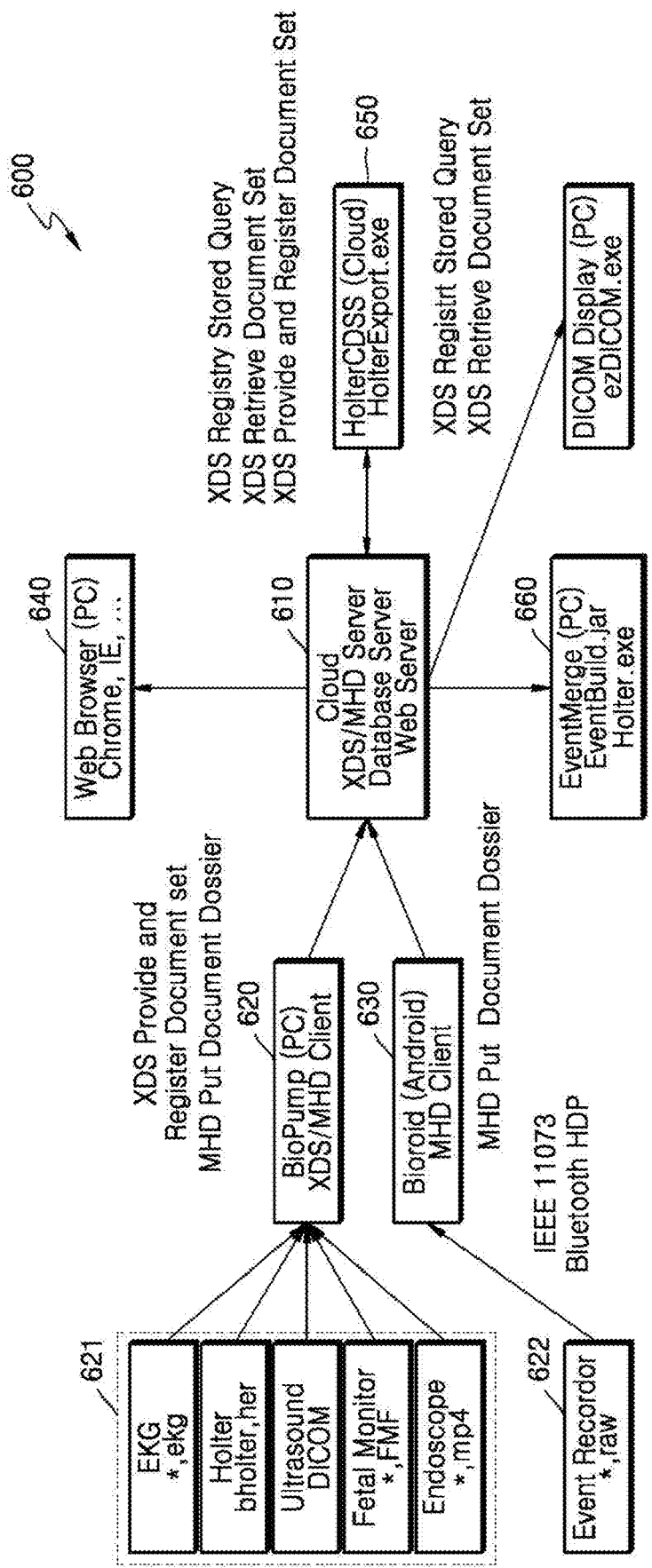
FIG. 6 is a diagram for explaining a communication protocol that is used in a system for providing medical information, according to an embodiment of the present invention.

FIG. 6 is a diagram for explaining a communication protocol that is used in a system 600 for providing medical information according to an embodiment of the present invention.

A cloud 610 included in the system 600 and programs 620 and 630 respectively installed in external apparatuses are illustrated in FIG. 6.

Each of the programs 620 and 630 may be any program as long as it may be connected to the cloud 610 through wired/wireless communication.

For example, the program BioPump 620 that transmits bio-signal information 621 to the cloud 610 and the cloud 610 may communicate with each other by using an IHE XDS or MHD protocol. In detail, the program BioPump 620 and the cloud 610 may communicate with each other by using an XDS Provide and Register Document Set protocol or an MHD Put Document Dossier protocol.

Also, in the program Bioroid 630 that receives bio-signal information 622 by using a file Event Recorder and re-transmits the bio-signal information to the cloud 610, an IHE MHD protocol suitable for a mobile environment may be used. An MEM protocol simplifies an XDS protocol to be suitable for a mobile environment.

A protocol used between the cloud 610 and the external filters 650 and 660 may also be an IRE XDS protocol. In detail, the cloud 610 and the external filters 650 and 660 may communicate with each other by using an XDS Registry Stored Query protocol, an XDS Retrieve Document Set protocol, or an XDS Provide and Register Document Set protocol.

The system 600 according to an embodiment of the present invention may use a general-purpose communication standard protocol. Accordingly, any API that is a standard protocol used in the system 600 may be connected to the cloud 640.

Main key values used when the programs 620 and 630 provided in external apparatuses communicate with the cloud 610 by using an XDS or MHD protocol are shown in Table 29.

TABLE 29

| Key | Description |
|---|---|
| entryUUID | Is a UUID of a document, and has to be completely unique. When first transmitted, a symbolic name, instead of a UUID, may be used. |
| classCode | Is a class code of a document. |
| creationTime | Is a time when the document is generated. |
| formatCode | Is a format code of the document. |
| mimeType | Indicates an MIME type of the document. |
| patientId | Indicates a patient number. |
| serviceStartTime | Indicates a time when a service starts. |
| sourcePatientInfo | Indicates a patient name, sex, birthdate, and address. |
| title | Is a title of the document. |
| typeCode | Is a type code of the document. |
| uniqueId | Is a UID of the document, and has to be unique in a group. |

TABLE 30

XDS/MHD Submission Set

| Key | Description |
|---|---|
| entryUUID | Is a UUID of a document set, and has to be completely unique. When firs transmitted, a symbolic name, instead of a UUID, may be used. |
| contentTypeCode | Is a code indicating content of the document set, and internally corresponds to a document set class UID. |
| patientId | Indicates a patient number. |
| sourceId | Indicates a source that generates the document set, and internally corresponds to a filter UID. |
| submissionTime | Indicates a time when the document set is transmitted. |
| title | Is a title of the document set. |
| uniqueId | Is a UID of the document set, and has to be unique in a group. |

According to the IHE XDS/MHD standard, a document, a document set, and a folder are realized and a relationship therebetween is expressed by using objects Document Entry, Submission Set, Folder, and Association. A database table structure for storing the objects in the cloud 610 is shown in Table 31 through Table 36.

TABLE 31

Table "Document"

| Column | Type | Modifiers | |
|---|---|---|---|
| document_key | integer | not null | PK |
| vgroup_key | integer | not null | FK, UK |

TABLE 31-continued

Table "Document"

| Column | Type | Modifiers | |
|---|---|---|---|
| document_uid | character varying(64) | not null | UK |
| repository_uid | character varying(64) | not null | UK |
| location_type | character varying(4) | | |
| location_root | character varying(256) | | |
| location_path | character varying(256) | | |
| document_size | integer | | |
| document_hash | character varying(256) | | |
| filter_key | integer | not null | FK |
| patient_key | integer | | FK |
| created_dttm | timestamp without time zone | not null | |
| deleted_dttm | timestamp without time zone | | |

TABLE 32

Table "XDSDocument"

| Column | Type | Modifiers | |
|---|---|---|---|
| xds_document_key | integer | not null | PK |
| document_key | integer | not null | FK |
| metadata_xml | xml | | |
| mime_type | character varying(128) | not null | |
| document_uuid | uuid | not null | UK |
| document_uid | character varying(64) | not null | |
| repository_uid | character varying(64) | not null | |
| document_status | character varying(1) | not null | default 'A' |
| patient_id | personid_t | | |
| source_patient_id | personid_t | | |
| document_title | character varying(128) | | |
| document_comments | character varying(4000) | | |
| author_id | personid_t | | |
| author_name | character varying(64) | | |
| class_code | codeinfo_t | | |
| format_code | codeinfo_t | | |
| h_f_type_code | codeinfo_t | | |
| language_code | character varying(256) | | |
| practice_code | codeinfo_t | | |
| type_code | codeinfo_t | | |
| service_start_dttm | timestamp without time zone | | |
| service_stop_dttm | timestamp without time zone | | |
| created_dttm | timestamp without time zone | not null | |
| deleted_dttm | timestamp without time zone | | |
| patient_name | character varying(256) | | |
| patient_sex | character varying(1) | | |
| patient_birth_dttm | timestamp without time zone | | |
| patient_address | character varying(256) | | |

TABLE 33

Table "DocSet"

| Column | Type | Modifiers | |
|---|---|---|---|
| docset_key | integer | not null | PK |
| vgroup_key | integer | not null | FK, UK |
| docset_uid | character varying(64) | not null | UK |
| docset_class_uid | character varying(64) | not null | FK |
| docset_group_uid | character varying(64) | not null | |
| filter_key | integer | not null | FK |
| patient_key | integer | | FK |
| created_dttm | timestamp without time zone | not null | |
| deleted_dttm | timestamp without time zone | | |

TABLE 34

Table "XDSDocSet"

| Column | Type | Modifiers | |
|---|---|---|---|
| xds_docset_key | integer | not null | PK |
| docset_key | integer | not null | FK |
| metadata_xml | xml | | |
| docset_uuid | uuid | not null | UK |
| docset_uid | character varying(64) | not null | |
| source_id | character varying(64) | not null | |
| patient_id | personid_t | | |
| content_type_code | codeinfo_t | | |
| docset_status | character varying(1) | not null | default 'A' |
| docset_title | character varying(128) | | |
| docset_comments | character varying(4000) | | |
| submit_dttm | timestamp without time zone | | |
| created_dttm | timestamp without time zone | not null | |
| deleted_dttm | timestamp without time zone | | |

TABLE 35

Table "XDSFolder"

| Column | Type | Modifiers | |
|---|---|---|---|
| xds_folder_key | integer | not null | PK |
| metadata_xml | xml | | |
| folder_uuid | uuid | not null | UK |
| folder_uid | character varying(64) | not null | |
| patient_id | personid_t | | |
| code_list | codeinfo_t[ ] | | |
| folder_status | character varying(1) | | |
| folder_title | character varying(128) | | |
| folder_comments | character varying(4000) | | |
| update_dttm | timestamp without time zone | | |
| created_dttm | timestamp without time zone | not null | |
| deleted_dttm | timestamp without time zone | | |

TABLE 36

Table "XDSAssociation"

| Column | Type | Modifiers | |
|---|---|---|---|
| xds_association_key | integer | not null | PK |
| metadata_xml | xml | | |
| association_uuid | uuid | not null | UK |
| association_kind | character varying(4) | not null | |
| association_type | character varying(16) | not null | |
| source_uuid | uuid | not null | |
| target_uuid | uuid | not null | |
| created_dttm | timestamp without time zone | not null | |

A correspondence between the tables of Table 31 through 36 and IRE XDS/MHD objects is shown in Table 37 through 40.

TABLE 37

| IHE XDS/MHD | Cloud database |
| --- | --- |
| DocumentEntry.entryUUID | XDSDocument.document_uuid |
| DocumentEntry.uniqueId | XDSDocument.document_uid |
| | Document.document_uid |
| DocumentEntry.hash | Document.hash |
| DocumentEntry.size | Document.size |
| DocumentEntry.repositoryUniqueId | XDSDocument.repository_uid |
| DocumentEntry.patientId | XDSDocument.patient_id |
| | Document.patient_key |
| | Document.vgroup_key |
| DocumentEntry.mimeType | XDSDocument.mime_type |
| DocumentEntry.status | XDSDocument.document_status |
| DocumentEntry.title | XDSDocument.document_title |
| DocumentEntry.comments | XDSDocument.document_comments |
| DocumentEntry.author | XDSDocument.author_id |
| | XDSDocument.author_name |
| DocumentEntry.sourcePatientId | XDSDocument.source_patient_id |
| DocumentEntry.sourcePatientInfo | XDSDocument.patient_name |
| | XDSDocument.patient_sex |
| | XDSDocument.patient_birth_dttm |
| | XDSDocument.patient_address |
| DocumentEntry.classCode | XDSDocument.class_code |
| DocumentEntry.formatCode | XDSDocument.format_code |
| DocumentEntry.healthcareFacilityTypeCode | XDSDocument.h_f_type_code |
| DocumentEntry.languageCode | XDSDocument.language_code |
| DocumentEntry.practiceSettingCode | XDSDocument.practice_code |
| DocumentEntry.typeCode | XDSDocument.type_code |
| DocumentEntry.creationTime | XDSDocument.created_dttm |
| DocumentEntry.serviceStartTime | XDSDocument.service_start_dttm |
| DocumentEntry.serviceStopTime | XDSDocument.service_stop_dttm |
| Document | Document.location_type |
| | Document.location_root |
| | Document.location_path |

TABLE 38

| IHE XDS/MHD | Cloud database |
| --- | --- |
| SubmissionSet.entryUUID | XDSDocSet.docset_uuid |
| SubmissionSet.uniqueId | XDSDocSet.docset_uid |
| | DocSet.docset_uid |
| SubmissionSet.patientId | XDSDocSet.patient_id |
| | DocSet.patient_key |
| | DocSet.vgroup_key |
| SubmissionSet.sourceId | XDSDocSet.source_id |
| | DocSet.filter_key |
| SubmissionSet.contentTypeCode | XDSDocSet.content_type_code |
| | DocSet.docset_class_uid |
| SubmissionSet.status | XDSDocSet.docset_staus |
| SubmissionSet.title | XDSDocSet.docset_title |
| SubmissionSet.comments | XDSDocSet.docset_comments |
| SubmissionSet.submissionTime | XDSDocSet.submit_dttm |

TABLE 39

| IHE XDS/MHD | Cloud database |
| --- | --- |
| Folder.entryUUID | XDSFolder.folder_uuid |
| Folder.uniqueId | XDSFolder.folder_uid |
| Folder.patientId | XDSFolder.patient_id |
| Folder.status | XDSFolder.folder_status |
| Folder.title | XDSFolder.folder_title |
| Folder.comments | XDSFolder.folder_comments |
| Folder.codeList | XDSFolder.code_list |
| Folder.lastUpdateTime | XDSFolder.update_dttm |

TABLE 40

| IHE XDS/MHD | Cloud database |
| --- | --- |
| Association.uuid | XDSAssociation.association_uuid |
| Association.sourceObject | XDSAssociation.source_uuid |

TABLE 40-continued

| IHE XDS/MHD | Cloud database |
| --- | --- |
| Association.targetObject | XDSAssociation.target_uuid |
| Association.associationType | XDSAssociation.association_type |
| | HAS: hasMember |
| | APND: append |
| | RPLC: replace |
| | XFRM: transform |
| | XFRM_RPLC: transformWithReplace |
| | SIGNS: signs |
| | XDSAssociation.association_kind |
| | SD: SubmissionSet - Original Document |
| | SE: SubmissionSet - Existing Document |
| | SF: SubmissionSet - Folder |
| | FD: Folder - Document |
| | DD: Document - Document |
| | JS: FilterJob - SubmissionSet |
| | JD: FilterJob - Document |

The external filters 650 and 660 perform an operation through five steps. The five steps through which the external filters 650 and 660 perform the operation are as follows.

In a first step, an operation that is to be performed in the external filters 650 and 660 is generated. In detail, when a filter operation is needed according to a filter condition, the cloud 610 generates a filter queue UUID and a filter queue input UUID in a filter queue (that is, tables of Table 25 and 27).

In a second step, the operation that is to be performed by the external filters 650 and 660 is searched for. For example, the operation that is to be performed by the external filters 650 and 660 may be searched for by using an XDS Registry Stored Query method. In detail, a stored query FindFilter-Jobs may change a filter operation into an association list as shown in Table 41.

TABLE 41

| Cloud database | IHE XDS/MHD |
|---|---|
| FilterQueueInput.filter_queue_input_uuid | Association.uuid |
| FilterQueue.filter_queue_uuid | Association.sourceObject |
| XDSDocSet.docset_uuid | Association.targetObject |

In a third step, a list of operations that are to be performed by the external filters 650 and 660 is prepared. For example, an association list of searched filter operations forms a filter job list in a program FilterProc as shown in Table 42.

TABLE 42

| IHE XDS/MHD | FilterProc.FilterJob |
|---|---|
| Association.uuid | FilterJob.docsetList.subjobUUID<br>= FilterQueueInput.filter_queue_input_uuid |
| Association.sourceObject | FilterJob.jobUUID<br>= FilterQueue.filter_queue_uuid |
| Association.targetObject | FilterJob.docsetList.docsetUUID<br>= XDSDocSet.docset_uuid |

The program FilterProc used herein refers to an interface module for realizing the external filters 650 and 660. In other words, the program FilterProc is needed to realize the external filters 650 and 660 that operate in the medical information providing system and designates a method of processing a specific filter/document set. The program FilterProc performs a designated operation according to content stored in a setting file after accessing the cloud by using designated server and port information.

If there is no query file additionally designated in addition to the setting file, a filter designated by a filter UID of the setting file is specified to perform an operation. If there is an additionally query file, filter processing is performed according to content designated in the query file.

Key values that may be used in a filter procedure setting file and a description thereof are shown in Table 43.

TABLE 43

| Key | Description |
|---|---|
| logLevel | Indicates a log level and designates one of the following values.<br>  OFF<br>  ERROR<br>  WARN<br>  INFO (default)<br>  DEBUG |
| serverHost | Is an address of a XDS/MHD server of a cloud. |
| serverPort | Is a port number of the XDS/MHD server of the cloud. |
| workingDir | Designates a working directory. |
| filenameFormat | Designates a file name of documents that are to be downloaded and may use the following keyword.<br>  %uid: is replaced by a UID of a document.<br>  %dttm: is replaced by a time when the document is generated.<br>  %seq: is replaced by a serial number that is automatically assigned. |
| retrieveSetCount | Indicates a set count when documents are downloaded. An HTTP overhead decreases as the set count increases. However, if the set count is too large, it exceeds a buffer capacity and thus the documents may fail to be downloaded. A default value is 1. |
| preprocessor | Designates when all of document sets are downloaded and then pre-processing is needed, and may use the following keyword.<br>  %inDocSetDir: is replaced by a folder name of an input document set. |

TABLE 43-continued

| Key | Description |
|---|---|
| |   %inDocSetPathList: is replaced by a path name list of all of document files included in the input document set.<br>  %inDocSetFileList: is replaced by a file name list of the all documents included in the input document set.<br>  %outDocSetDir: is replaced by a folder name of an output document set. |
| processor | Designates a path name and factors called for a document or a document set, and may additionally use the following keyword in addition to the keyword designated in the above preprocessor.<br>  %inDocFile: is replaced by a file name of an individual input document.<br>  %inJobDir: is replaced by an overall operation folder when two or more input document sets are needed for filter processing.<br>  %inJobPathList: is replaced by an overall path name list of all input document files included in an operation folder.<br>  %inJobFileList: is replaced by a file name list of the all input documents included in the operation folder.<br>  %outDocFile: is replaced by a name of an individual output document file.<br>  %outJobDir: is replaced by a name of an output operation folder. |
| postprocessor | Designates when document set processing is completed and then post-processing is needed, and may use the same keyword as that of the preprocessor. |
| filterUID | Designates a UID of a filter. |
| UIDPrefix | Refers to a prefix for UIDs that are generated for metadata. |
| groupIdType | Indicates a group ID type and uses "BIS-CLOUD" in a BIS-Cloud unless there is a special reason. |
| docsetClassUID | Refers to a class UID value for generated document sets. |
| docsetTitle | Is a default title for the generated document sets. |
| docsetComments | Is a default description of the generated document sets. |
| mimeType | Is an MIME type that is needed to upload a generated document. |
| rename | Determines whether documents having used in an operation are to be moved or deleted, and designates true to move the documents and false to delete the documents. A default value is false (delete). |
| repeat | Determines whether to repeat. A default value is false (no repetition). |
| repeatInterval | Designates a repetition interval. For example, 300 (seconds) may be designated as a repetition interval. |

A program FilterProc generates an operation folder under a folder designated with a working directory workingDir as shown in Table 44. The program FilterProc may designate that pieces of content of the operation folder are to be deleted later.

TABLE 44

| Folder/Filename | Description |
|---|---|
| {workingDir}/FJ-xxxx | Input operation folder |
| {workingDir}/FJ-xxxx/output | Output operation folder |
| {workingDir}/FJ-xxxx/DS-yyyy | Input document set folder |
| {workingDir}/FJ-xxxx/DS-yyyy/output | Output document set folder |
| {workingDir}/FJ-xxxx/DS-yyyy/zzzz | Input document file |
| {workingDir}/FJ-xxxx/DS-yyyy/zzzz.xml | Input document metadata (XDS Document Entry) |
| {workingDir}/FJ-xxxx/DS-yyyy/zzzz.output | Output document file |
| {workingDir}/FJ-xxxx/DS-yyyy/DS.xml | Input document set metadata (XDS Submission Set) |

In a fourth step, the external filters 650 and 660 transmit a result of the operation to the cloud 610. In this case, the external filters 650 and 660 transmit association information as shown in Table 45 before transmitting a document set that is a result of the operation to the cloud 610.

TABLE 45

| FilterProc.FilterResult | IHE XDS/MHD |
| --- | --- |
| Auto-generated | Association.uuid |
| Created XDSDocSet.docset_uuid or XDSDocument.document_uuid | Association.sourceObject |
| FilterJob.docsetList.subjobUUID = FilterQueueInput.filter_queue_input_uuid | Association.targetObject |
| APND | Association.associationType |
| "FilterJobStatus" | Association.slotName |
| "SubmissionSet" or "DocumentEntry" | Association.slotValue |

In a fifth step, the external filters 650 and 660 complete the operation. An XDS server XDSServer of the cloud 610 according to an embodiment of the present invention first stores Association.slotName="FilterJob Status" in a database before storing the objects DocumentEntry, SubmissionSet, Folder, and Association in the database. In this case, a association_kind column value of an XDSAssociation table is determined according to an Association.slotValue. Then, the XDS server XDSServer stores attributes of the object Association in the database and finally calls a function FilterQueue_update( ) to record that the filter operation is completed. An example is shown in Table 46.

TABLE 46

| IHE XDS/MHD | Cloud database |
| --- | --- |
| Association.uuid | XDSAssociation.association_uuid |
| Association.sourceObject = Created XDSDocSet.docset_uuid/ XDSDocument.document_uuid | XDSAssociation.source_uuid |
| Association.targetObject = FilterJob.docsetList.subjobUUID = FilterQueueInput.filter_queue_input_uuid | XDSAssociation.target_uuid |
| Association.associationType = "APND" | XDSAssociation.association_type |
| Association.slotName = "FilterJobStatus" | |
| Association.slotValue = "SubmissionSet" = "DocumentEntry" | XDSAssociation.association_kind JS (FilterJob - SubmissionSet) JD (FilterJob - Document) |

The external filter HolterCDSS 650 that is one external filter provided in the cloud 610 downloads a radionet holter file from the cloud 610 and performs a program HolterExport.exe or Holter.exe to perform CDSS processing. The external filter HolterCDSS 650 uploads again automatic diagnosis result files having a JPEG format generated as a result of the program to the cloud 650.

The external filter HolterCDSS 650 is a batch file made based on the program FilterProc and includes, in detail, a FilterProc.jar module that is in charge of communicating with the cloud and a HolterExport.exe or Holter.exe module that is in charge of performing actual CDSS processing.

A configuration and setting of the external filter HolterCDSS 650 according an embodiment of the present invention are respectively shown in Table 47 and Table 48.

TABLE 47

Configuration: HolterCDSS.bat

@ECHO OFF
SET BIS_DIR=C:\OPHIES
SET LIB_DIR=%BIS_DIR%\lib

TABLE 47-continued

Configuration: HolterCDSS.bat

SET CONFIG_FILE=%BIS_DIR%\bin\HolterCDSS.conf
java -jar %LIB_DIR%\FilterProc.jar -conf %CONFIG_FILE% %1

TABLE 48

Setting: HolterCDSS.conf

{
  "FilterProc" : {
    "logLevel" : "INFO",
    "serverHost" : "54.238.177.162",
    "serverPort" : "8080",
    "workingDir" : "C:/OPHIES/work",
    "filenameFormat" : "%uid",
    "retrieveSetCount" : "3",
    "preprocessor" : "",
    "processor" : "\"C:\\Program Files\\RADIONET\\Holter\\Holter.exe\" -hrw2jpg %inDocFile %outJobDir",
    "postprocessor" : "",
    "filterUID" : "1.2.410.200054.4.2.1",
    "UIDPrefix" : "1.2.410.200054",
    "groupIdType" : "BIS-CLOUD",
    "docsetClassUID" : "1.2.410.200054.5.2.1",

TABLE 48-continued

Setting: HolterCDSS.conf

"docsetTitle" : "HolterExport Results",
    "docsetComments" : "%cmdline",
    "mimeType" : "image/jpeg",
    "rename" : "false",
    "repeat" : "true",
    "repeatInterval" : "60",
  }
}

The external filter EventMerge 660 is one external filter provided in the cloud 610, and downloads signal files Event Recorder stored in the cloud 610, merges and changes the signal files Event Recorder, and transmits the merged signal files as an input to a program Holter.exe.

The external filter EventMerge 660 is a batch file made based on the program FilterProc, and includes, in detail, EventBuild.jar that is a preprocessor for merging the signal files Event Recorder and Holter.exe for processing actual holter information.

In order to operate the external filter EventMerge 660, a query file as shown in the following has to be generated and transmitted as a factor. In this case, GetSubmissionSetAnd- Contents has to be designated as a query type and a UID of a document set docsetUID containing files Event Recorder to be merged has to be designated. Such query files may be obtained by being downloaded from a document set list of a web browser 640.

A configuration and setting of the external filter Event-Merge 660 according to an embodiment of the present invention are respectively shown in Table 49 and Table 50.

TABLE 49

Configuration: EventMerge.bat

```
@ECHO OFF
SET BIS_DIR=D:\OPHIES
SET LIB_DIR=%BIS_DIR%\lib
SET CONFIG_FILE=%BIS_DIR%\bin\EventMerge.conf
java -jar %LIB_DIR%\FilterProc.jar -conf %CONFIG_FILE% %1
```

TABLE 50

Setting: EventMerge.conf

```
{
  "FilterProc" : {
    "logLevel" : "INFO",
    "serverHost" : "54.238.177.162",
    "serverPort" : "8080",
    "workingDir" : "D:/Temp",
    "filenameFormat" : "%dttm.raw",
    "retrieveSetCount" : "3",
    "preprocessor" : "java -jar
D:/OPHIES/lib/EventBuild.jar %inDocSetDir",
    "processor" : "\"C:\\Program Files\\RADIONET\\Holter\\Holter.exe\"
-evt %inDocSetDir",
    "rename" : "false",
  }
}
```

Figure 7:
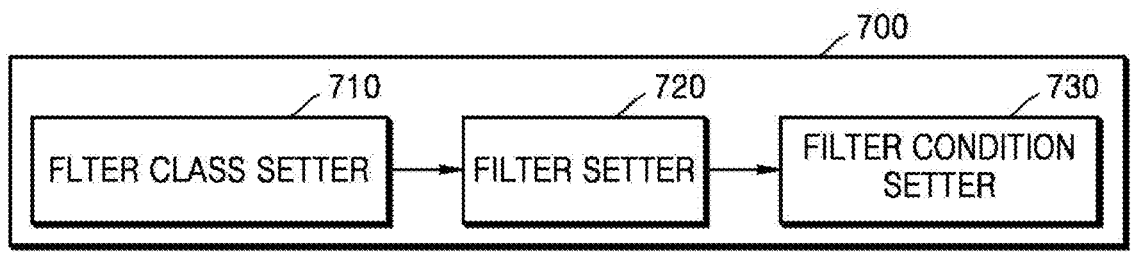
FIG. 7 is a diagram illustrating an apparatus for generating information about a filter, according to an embodiment of the present invention.

FIG. 7 is a diagram illustrating an apparatus 700 for generating information about a filter according to an embodiment of the present invention.

Referring to FIG. 7, the apparatus 700 includes a filter class setter 710, a filter setter 720, and a filter condition setter 730. Only elements related to the present embodiment are illustrated in the apparatus 700 of FIG. 7. Accordingly, it will be understood by one of ordinary skill in the art that general-purpose elements other than the elements illustrated in FIG. 7 may be further included in the apparatus 700.

Also, the filter class setter 710, the filter setter 720, and the filter condition setter 730 of FIG. 7 may correspond to one or a plurality of processors. Each processor may be an array of logic gates, or a combination of a general-purpose microprocessor and a memory storing a program that may be executed by the microprocessor. Also, it will be understood by one of ordinary skill in the art that the processor may be another type of hardware.

Also, the apparatus 700 of FIG. 7 may be further included in the medical information providing system or the cloud of FIGS. 1, 2, 5, and 6. Accordingly, although omitted, the description of the medical information providing system or the cloud of FIGS. 1, 2, 5, and 6 may apply to the apparatus 700 of FIG. 7.

The filter class setter 710 sets at least one filter class corresponding to an operation for generating medical information of an object. The object used herein may refer to, but not limited to, a patient. The filter class refers to a class of a filter and an input/output method is expressed by using a document set class. One filter class may correspond to a plurality of filters. That is, there may be various filters having the same input/output method and function.

The filter setter 720 sets at least one filter that is included in the filter class and performs an operation. Types of the filter include an internal filter and an external filter. The internal filter may refer to a filter that performs an operation in a database of the cloud and may be a stored function of a database of an infrastructure. The external filter may refer to a filter that performs an operation outside the database of the cloud and may be realized by using an API provided by the cloud.

The filter indicates an instance of the filter and indicates an actual instance of the filter expressed with a filter class. All filters having the same filter class UID may perform substantially the same function.

An operation performed by the filter may correspond to any one from among an operation of converting at least one input content into at least one output content, an operation of storing content, an operation of providing content to another apparatus, and an operation of generating content. The other apparatus to which the content is provided refers to an apparatus for using the content in various ways, for example, an apparatus for displaying the content.

The content used herein refers to any type of document including text, an image, or a video. In other words, examples of the content may include all types of documents, such as images, waveforms, and measured values, which may be processed by general arithmetic units. Accordingly, content and a document in the description of FIGS. 1 through 6 are expressed as the same concept.

The condition setter 730 sets at least one condition required to operate the filter. In detail, the condition setter 730 sets a filter that is to perform an operation, and sets information required to operate the filter and/or a time condition corresponding to a time when the filter performs the operation. The time condition corresponds to any one from among a condition in which the filter performs the operation when information is input to the filter, a condition in which the filter performs the operation a predetermined period of time after information is input, and a condition in which the filter performs the operation a predetermined period of time after the beginning (00:00 A.M.) of the day after information is input.

Figure 8:
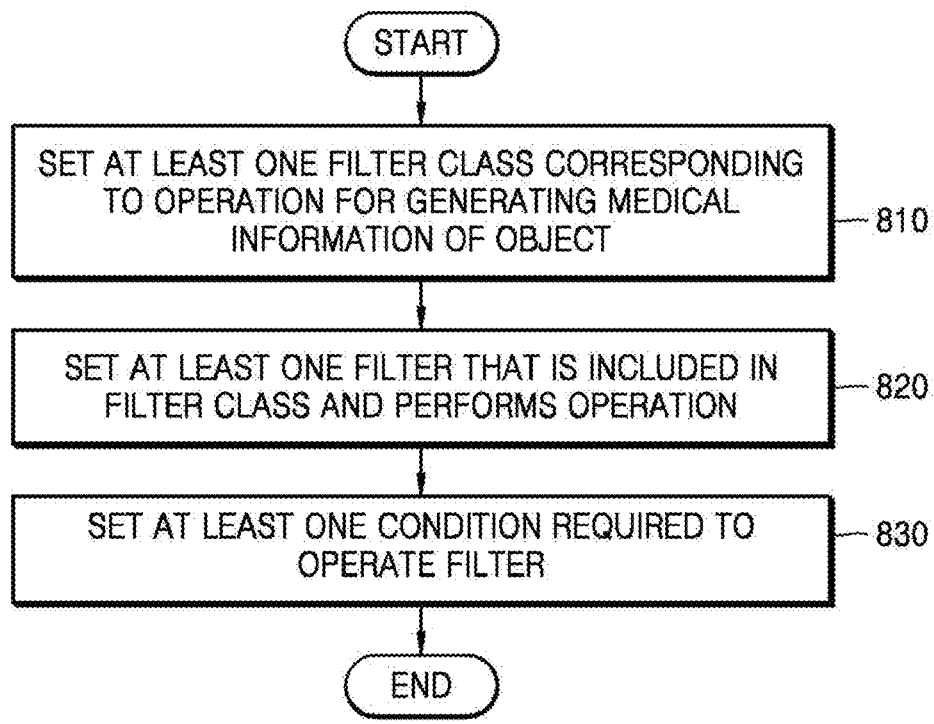
FIG. 8 is a flowchart illustrating a method of generating information about a filter, according to an embodiment of the present invention.

FIG. 8 is a flowchart illustrating a method of generating information about a filter (referred to as the filter information generating method) according to an embodiment of the present invention.

Referring to FIG. 8, the filter information generating method includes steps that are sequentially performed by the medical information providing system, the cloud, or the apparatus 700 of FIGS. 1, 2, 5, 6, and 7. Accordingly, although omitted, the description made with reference to FIGS. 1, 2, 5, 6, and 7 may apply to the filter information generating method of FIG. 8.

In step 810, a cloud sets at least one filter class corresponding to an operation for generating medical information of an object.

In step 820, the cloud sets at least one filter that is included in the filter class and performs an operation.

In step 830, the cloud sets at least one condition required to operate the filter.

Figure 9:
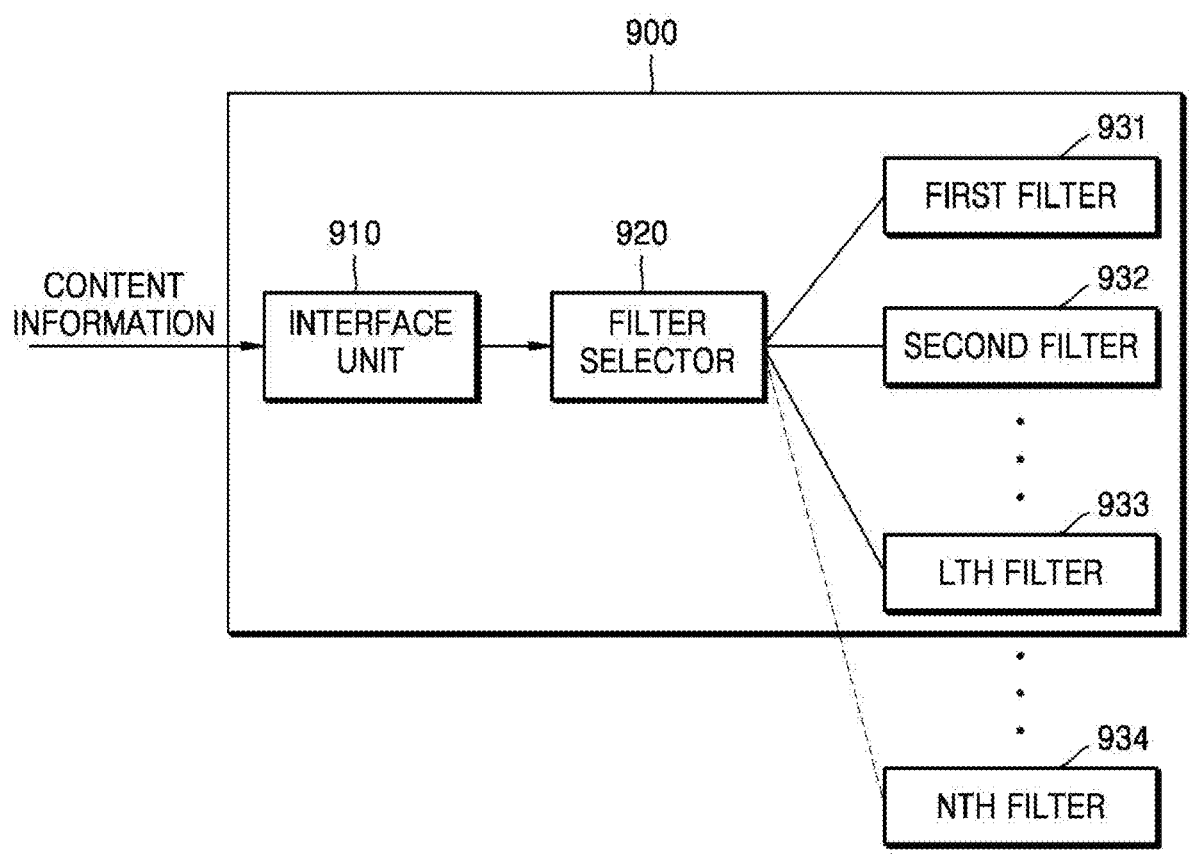
FIG. 9 is a diagram illustrating an apparatus for generating medical information of an object, according to an embodiment of the present invention.

FIG. 9 is a diagram illustrating an apparatus 900 for generating medical information of an object according to an embodiment of the present invention.

Referring to FIG. 9, the apparatus 900 includes an interface unit 910, a filter selector 920, and a plurality of internal filters 931, 932, and 933. Also, at least one filter may exist as an external filter 934 that is not included in the apparatus 900. Only elements related to the present embodiment are illustrated in the apparatus 900 of FIG. 9. Accordingly, it will be understood by one of ordinary skill in the art that general-purpose elements other than the elements of FIG. 9 may be further included in the apparatus 900.

Also, the interface unit 910 and the filter selector 920 included in the apparatus 900 of FIG. 9 may correspond to one or more processors. Each processor may be an array of logic gates, or a combination of a general-purpose microprocessor and a memory storing a program that may be executed by the microprocessor. Also, it will be understood by one of ordinary skill in the art that the processor may be another type of hardware.

Also, the apparatus 900 of FIG. 9 may be included in the medical information providing system or the cloud of FIGS. 1, 2, 5, and 6. Accordingly, although omitted, the description of the medical information providing system or the cloud of FIGS. 1, 2, 5, and 6 may apply to the apparatus 900 of FIG. 7.

The interface unit 910 receives at least one content from at least one from among external apparatuses connected to the cloud. Content used herein refers to any type of document including text, an image, or a video. In other words, examples of the content may include all types of documents, such as images, waveforms, and measured values, which may be processed by general arithmetic units. Accordingly, content and a document in the description of FIGS. 1 through 6 are expressed as the same concept.

The filter selector 920 selects a filter that performs a preset operation based on the content received by the interface unit 910 from among filters respectively included in a plurality of filter classes. A filter class refers to a class of a filter, and an input/output method is expressed by using a document set class. One filter class may correspond to a plurality of filters. That is, there may be various filters having the same input/output method and function.

Types of the filter include an internal filter and an external filter. The internal filter may refer to a filter that performs an operation in a database of the cloud and may be a stored function of a database of an infrastructure. The external filter may refer to a filter that performs an operation outside the database of the cloud and may be realized by using an API provided by the cloud.

The preset operation performed by the filter selected by the filter selector 920 refers to any one from among an operation of converting at least one input content into at least one output content, an operation of providing content to at least one from among apparatuses connected to the cloud, an operation of generating new content by combining different pieces of content, and an operation of storing content. The apparatus to which the content is provided refers to an apparatus for using the content in various ways, for example, an apparatus for displaying the content.

Also, the filter selector 920 may select a filter that performs an operation based on a result of the preset operation from among the filters respectively included in the plurality of filter classes. In other words, as shown in the workflow of FIG. 4, the filter selector 920 may select another filter that performs another operation by using a result of the operation of the filter.

Information required to operate each of the internal filters 931, 932, and 933 and the external filter 934 and/or a time condition corresponding to a time when the filter performs an operation are set. The time condition may correspond to any one from among a condition in which the filter performs the operation when information is input to the filter, a condition in which the filter performs the operation a predetermined period of time after information is input, and a condition in which the filter performs the operation a predetermined period of time after the beginning (00:00 A.M.) of the day after information is input.

Figure 10:
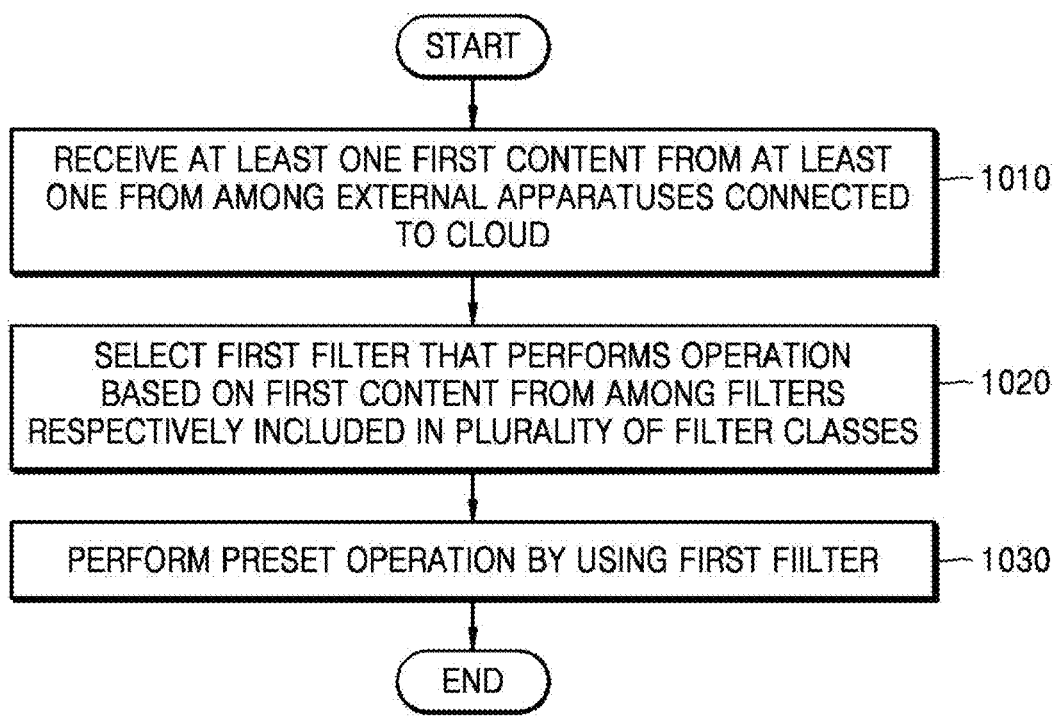
FIG. 10 is a flowchart illustrating a method of generating medical information of an object, according to an embodiment of the present invention.

FIG. 10 is a flowchart illustrating a method of generating medical information of an object (referred to as the object medical information generating method) according to an embodiment of the present invention.

Referring to FIG. 10, the filter information generating object medical information generating method includes steps that are sequentially processed by the medical information providing system, the cloud, or the apparatus 900 of FIGS. 1, 2, 5, 6, and 9. Accordingly, although omitted, the description made with reference to FIGS. 1, 2, 5, 6, and 9 may apply to the object medical information generating method of FIG. 10.

In step 1010, a cloud receives at least one content from at least one from among external apparatuses connected to the cloud.

In step 1020, the cloud selects a filter that performs an operation based on received content from among filters respectively included in a plurality of filter classes.

In step 1030, the selected filter performs a preset operation.

The afore-described method may be implemented as an executable program, and may be executed by a general-purpose digital computer that runs the program by using a computer-readable recording medium. Also, a structure of data used in the method may be recorded by using various units on a computer-readable recording medium. Examples of the computer-readable recording medium include storage media such as magnetic storage media (e.g., read-only memories (ROMs), random-access memories (RAMs), universal serial buses (USBs), floppy discs, or hard discs), optically readable media (e.g., compact disk-read only memories (CD-ROMs), or digital versatile disks (DVDs)), etc.

Numerous modifications and adaptations will be readily apparent to one of ordinary skill in this art from the detailed description and the embodiments without departing from the spirit and scope of the present invention. The methods should be considered in a descriptive sense only and not for purposes of limitation. Therefore, the scope of the present invention is defined not by the detailed description of the invention but by the appended claims, and all differences within the scope will be construed as being included in the present invention.

The invention claimed is:

1. A method of generating information about a filter, the method comprising:
identifying, by a dataset handler included in a cloud, a workflow for generating a first document set (DS), storing a second DS, and providing a third DS to another apparatus which is configured to display the third DS;
setting, by the data handler included in the cloud, at least one document set class (DSC) corresponding to each of the first DS, the second DS, the third DS, a fourth DS and a fifth DS, by identifying a UID of the first DS to the fifth DS;
setting, by a filter class setter included in the cloud, at least one filter class by specifying an input/output format corresponding to the at least one DSC
setting, by the filter setter included in the cloud, at least one filter by identifying a default group of each filter included in the filter class and retrieving the at least one filter configured to perform the workflow; and setting, by the filter rule setter apparatus included in the cloud, at least one condition required to operate the at least one filter, wherein the setting of the condition includes setting DS information required to operate the filter and a time condition corresponding to a time when the filter performs the operation, and wherein the time condition comprises any one from among (i) a first condition in which the operation is performed when the DS information required to operate the filter is input to the filter, (ii) a second condition in which the operation is performed a predetermined period of time after the DS information required to operate the filter is input, and (iii) a third condition in which the operation is performed a predetermined period of time after a given time of day after the information required to operate the filter is input.

2. The method of claim 1, wherein the operation comprises any one from among a first operation of converting at least one first content into at least one second content, a second operation of storing third content, a third operation of providing fourth content to another apparatus, and a fourth operation of generating fifth content.

3. The method of claim 2, wherein the content comprises any one from among text, an image, a video, a waveform, and a general document.

4. An apparatus in a cloud system for generating information about a filter, the apparatus comprising:

a data handler configured to identify a workflow for generating a first document set (DS), storing a second DS, and providing a third DS to another apparatus which is configured to display the third DS, wherein the data handler is further configured to set at least one document set class (DSC) corresponding to each of the first DS, the second DS, the third DS, a fourth DS, and a fifth DS, by identifying UID of the first DS to the fifth DS;

a filter class setter configured to set at least one filter class by specifying an input/output format corresponding to at least one DSC;

a filter setter configured to set at least one filter by identifying a default group of each filter included in the filter class and retrieving the at least one filter configured to perform the workflow; and a filter rule setter configured to set at least one condition required to operate the at least one filter, wherein the filter rule setter is further configured to set DS information required to operate the filter and a time condition corresponding to a time when the filter performs the operation, and wherein the time condition comprises any one from among a first condition in which the operation is performed when the DS information required to operate the filter is input to the filter, a second condition in which the operation is performed a predetermined period of time after the DS information required to operate the filter is input, and a third condition in which the operation is performed a predetermined period of time after a given time of day after the information required to operate the filter is input.

5. The apparatus of claim 4, wherein the operation comprises any one from among a first operation of converting at least one first content into at least one second content, a second operation of storing third content, a third operation of providing fourth content to another apparatus, and a fourth operation of generating fifth content.

6. The apparatus of claim 5, wherein the content comprises any one from among text, an image, a video, a waveform, and a general document.

* * * * *